United States Patent
Phillips et al.

(10) Patent No.: US 9,216,983 B2
(45) Date of Patent: Dec. 22, 2015

(54) DIHYDROOROTATE DEHYDROGENASE INHIBITORS WITH SELECTIVE ANTI-MALARIAL ACTIVITY

(75) Inventors: Margaret Phillips, Dallas, TX (US); Pradipsinh K. Rathod, Seattle, WA (US); Ramesh Gujjar, Seattle, WA (US); Alka Marwaha, Seattle, WA (US); Susan A. Charman, Parkville (AU)

(73) Assignees: BOARD OF REGENTS, UNIVERSITY OF TEXAS SYSTEM, Austin, TX (US); UNIVERSITY OF WASHINGTON, Seattle, WA (US); MONASH UNIVERSITY, Victoria (AU)

( * ) Notice: Subject to any disclaimer, the term of this patent is extended or adjusted under 35 U.S.C. 154(b) by 1103 days.

(21) Appl. No.: 12/339,905

(22) Filed: Dec. 19, 2008

(65) Prior Publication Data
US 2009/0209557 A1 Aug. 20, 2009

Related U.S. Application Data

(60) Provisional application No. 61/015,928, filed on Dec. 21, 2007, provisional application No. 61/036,264, filed on Mar. 13, 2008, provisional application No. 61/036,303, filed on Mar. 13, 2008, provisional application No. 61/111,575, filed on Nov. 5, 2008.

(51) Int. Cl.
C07D 487/04 (2006.01)
C07D 473/34 (2006.01)
A61K 31/519 (2006.01)

(52) U.S. Cl.
CPC ............ *C07D 487/04* (2013.01); *C07D 473/34* (2013.01)

(58) Field of Classification Search
CPC .................................................... C07D 487/04
USPC ...................... 544/263; 514/259.31
See application file for complete search history.

(56) References Cited

U.S. PATENT DOCUMENTS

| | | | |
|---|---|---|---|
| 6,096,753 A | 8/2000 | Spohr et al. | |
| 2003/0195221 A1 | 10/2003 | Cai et al. | |
| 2007/0155738 A1* | 7/2007 | Steeneck et al. | 514/230.5 |
| 2009/0118135 A1* | 5/2009 | Reed et al. | 506/9 |
| 2009/0163545 A1* | 6/2009 | Goldfarb | 514/312 |

FOREIGN PATENT DOCUMENTS

| FR | 1567021 | * | 5/1969 |
| WO | WO 01/34603 A2 | | 5/2001 |

OTHER PUBLICATIONS

Vippagunta, S.R., (Adv. Drug. Delivery Rev., 2001, 48, pp. 3-26).*
Banker, G.S. et al, "Modern Pharmaceutics, 3ed.", Marcel Dekker, New York, 1996, p. 596.*
Wolff, Manfred E. "Burger's Medicinal Chemistry, 5ed, Part I", John Wiley & Sons, 1995, pp. 975-977.*
Britsun et. al. (Russian Journal of Organic Chemistry, 2008, 44(10), pp. 1528-1531).*
Reynolds et al. (Journal of Organic Chemistry, 1961, 26, pp. 115-117).*
Camille G. Wermuth, "Molecular Variations Based on Isosteric Replacements", The Practice of Medicinal Chemistry, 1996, pp. 205-237.
David A. Fidock et al., "Antimalarial Drug Discovery: Efficacy Models for Compound Screening"Nature Reviews, vol. 3, Jun. 2004, pp. 509-520.
Joanna A. M. Braks et al., "Development and application of a positive—negative selectable marker system for use in reverse genetics in *Plasmodium*", Nucleic Acid Research, 2006, vol. 34, No. 5, 1-12.
Chris J. Janse et al., "High efficiency transfection of *Plasmodium bergei* facilitates novel selection procedures", Molecular and Biochemical Parasitology 145 (2006) pp. 60-70.
Jeffrey Baldwin et al., "Malarial Dihydroorotate Dehydrogenase", The Journal of Biological Chemistry, vol. 277, No. 44, Issue of Nov. 1, 2002, pp. 41827-41834.
Kai Zhang et al., "Divergent Regulation of Dihydrofolate Reductase Between Malaria Parasite and Human Host", Science, vol. 296, Apr. 19, 2002, pp. 545-547.
Robert E. Desjardins et al., "Quantitative Assessment of Antimalarial Activity in Vitro by a Semiautomated Microdiluation Technique", Antimicrobial Agents and Chemotherapy, vol. 16, No. 6, Dec. 1979, pp. 710-718.
Jeffrey Baldwin et al., "High-throughput Screening for Potent and Selective Inhibitors of*Plasmodium falciparum* Dihydroorotate Dehydrogenase", The Journal of Biological Chemistry, vol. 280, No. 23, Issue of Jun. 10, 2005, pp. 21847-21853.
Shinya Morimoto et al., "Rab13 mediates the continuous endocytic recycling of occludin to the cell surface." Additions and Corrections, The Journal of Biological Chemistry, vol. 280, No. 36, Issue of Sep. 9, 2005, pp. 32048.
Sarban Morosan et al., "Liver-Stage Development of *Plasmodium faciparum*, in a Humanized Mouse Model", JID Apr. 1, 2006, pp. 996-1004.
PCT International Search Report PCT/US08/87680 dated Feb. 24, 2009.

* cited by examiner

*Primary Examiner* — Susanna Moore
(74) *Attorney, Agent, or Firm* — Saliwanchik, Lloyd & Eisenschenk

(57) ABSTRACT

Compounds according to Formula I, Formula II, Formula III, Formula V, Formula VI, or to Formula VII, (I)

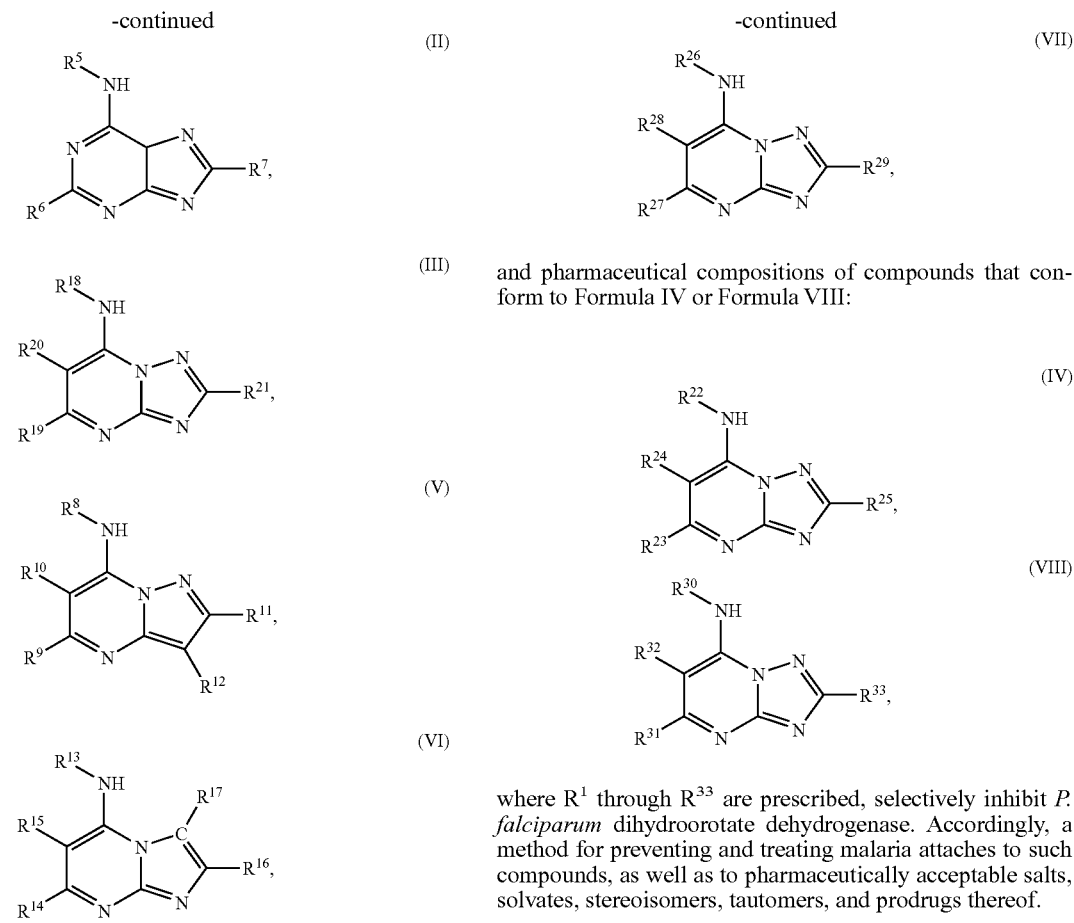

and pharmaceutical compositions of compounds that conform to Formula IV or Formula VIII:

where $R^1$ through $R^{33}$ are prescribed, selectively inhibit *P. falciparum* dihydroorotate dehydrogenase. Accordingly, a method for preventing and treating malaria attaches to such compounds, as well as to pharmaceutically acceptable salts, solvates, stereoisomers, tautomers, and prodrugs thereof.

7 Claims, 1 Drawing Sheet

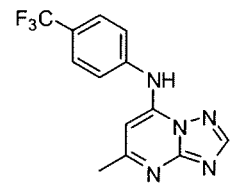
Figure 1A:
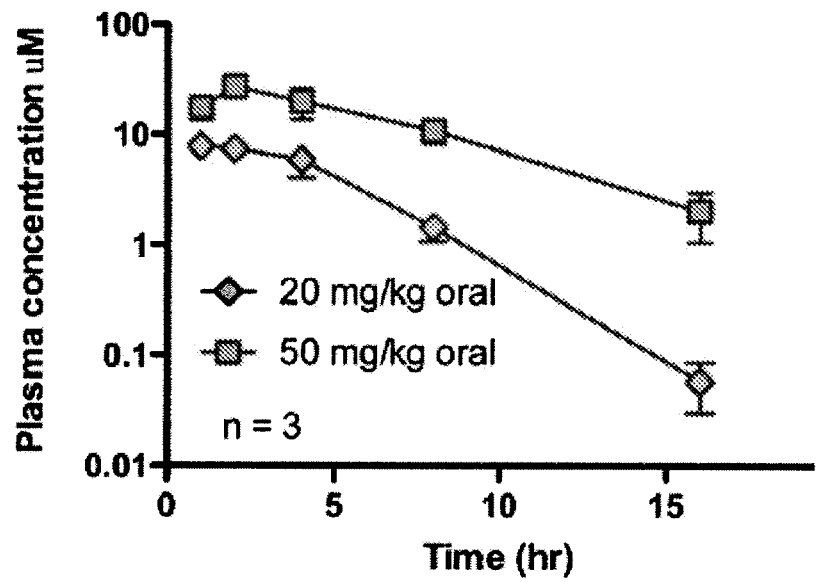
Figure 1B:
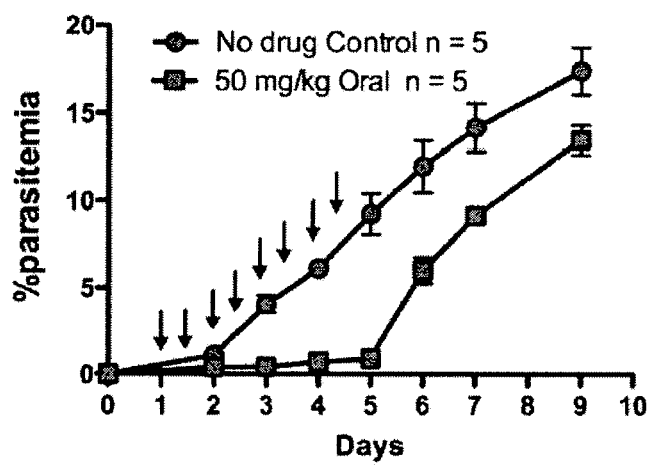

DIHYDROOROTATE DEHYDROGENASE INHIBITORS WITH SELECTIVE ANTI-MALARIAL ACTIVITY

This application claims the benefit of priority of U.S. Provisional Applications No. 61/015,928 filed on Dec. 21, 2007; No. 61/036,303 filed on Mar. 13, 2008; No. 61/036,264 filed on Mar. 13, 2008, and No. 61/111,575 filed on Nov. 5, 2008.

GOVERNMENT RIGHTS

This invention was funded by NIH R01 AI053680 and NIH UO1 AI075594. The U.S. Government has certain rights in this invention.

BACKGROUND OF THE INVENTION

The present invention relates generally to novel anti-malarial agents and inhibitors of dihydroorotate dehydrogenase.

Malaria infects up to 900 million people and causes as many as 2.7 million deaths worldwide every year. Nearly 40% of the world population is at risk for contracting this disease, which has been a major cause of mortality throughout history. In the United States travelers to these endemic regions are at risk for contracting the disease. The widespread emergence of drug resistance in many tropical countries has compromised many of the current chemotherapies and there is a continued need for new chemotherapeutic approaches.

Malaria is a disease caused by a parasite transmitted by the bite of an infected female *Anopheles* mosquito. When an infecting sporozoite parasite enters the bloodstream it rapidly infects both liver and red blood cells and differentiates into merozoites. Asexual reproduction of the merozoite within erythrocytes results in the rupture and subsequent reinfection of other red blood cells. This cyclic process results in clinical symptoms, which include headaches, sweating, vomiting, malaise, delirium and acute fever and may be fatal if not treated. Malaria in humans is caused by 4 species of parasitic protozoa belonging to the genus *Plasmodium*. Of these, *P. falciparum* is the most deadly and the greatest threat to travelers abroad while *P. malariae*, *P. vivax* and *P. ovale*, though infrequently fatal in healthy adults, can cause morbidity in the endemic areas.

Various medications are presently used for the treatment of malaria. However, many of these medications are costly and some exhibit significant toxicity and undesirable side effects in humans. The most common drug for treating malaria is chloroquine. Other drugs include quinine, mefloquine, atovaquone/proguanil, doxycycline, artesunate, hydroxychloroquine, halofantrine, pyrimethamine-sulfadoxine, and primaquine. Drug choice often depends on one of the four types of malaria parasites.

Malaria parasites rely on de novo pyrimidine biosynthesis to provide precursors for DNA and RNA synthesis, hence for proliferation. The parasite does not have pyrimidine nucleoside or base salvage pathways, thus the enzymes in the de novo pathway are essential to parasite survival. In contrast, mammalian cells have salvage pathways that provide an alternative route to these essential metabolites.

Dihydroorotate dehydrogenase (DHODH) is an essential enzyme for the salvage pathway, and a number of lines of evidence suggest that it is an important target for the development of new chemotherapy against malaria. DHODH is a flavin-dependent mitochondrial enzyme that catalyzes the fourth reaction in the salvage pathway; coenzyme Q is utilized as the oxidant. The enzyme has a number of properties that make it a particularly strong candidate as a new drug target in the parasite. Inhibitors of human DHODH have proven efficacy for the treatment of rheumatoid arthritis demonstrating that the target pathway can be effectively blocked in vivo. The X-ray structures of DHODH reveal that the inhibitor binding pocket of the enzyme is highly variable between species, providing a structural basis for the design of species-specific inhibitors.

A need exists for a method of treating malaria. There is also a need for an anti-malarial agent to overcome current drug resistance problems with existing therapy. Further, anti-malarial agents are needed that selectively inhibit malarial DHODH but exhibit no substantial toxicity against mammalian, especially human DHODH.

Accordingly, this invention provides novel potent anti-malarial agents and methodology of treating malaria using novel potent anti-malarial agents. The invention also provides potent anti-malarial agents that are selective inhibitors of *P. falciparum* dihydroorotate dehydrogenase and active against chloroquine-sensitive and resistant malarial strains.

SUMMARY OF THE INVENTION

The present invention relates to novel compounds for inhibiting the activity of *Plasmodium falciparum* dihydroorotate dehydrogenase. The compounds display selective inhibition of *Plasmodium falciparum* dihydroorotate dehydrogenase over human dihydroorotate dehydrogenase.

The present invention also relates to methods for preventing or treating diseases associated with the action of *Plasmodium falciparum* dihydroorotate dehydrogenase, such as malaria.

In accordance with the invention, compounds are provided that conform to Formula I, Formula II, Formula III, Formula V, Formula VI, or to Formula VII.

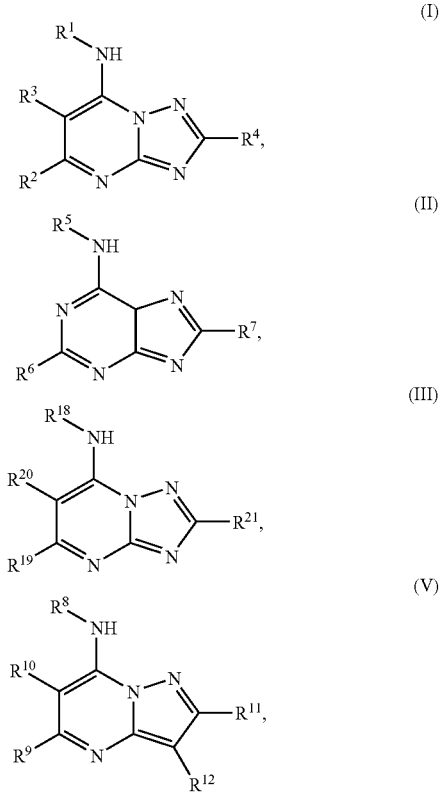

-continued

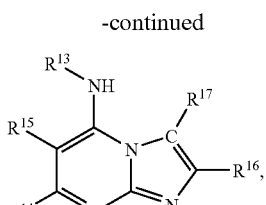

(VI)

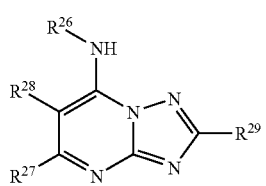

(VII)

The invention also encompasses pharmaceutically acceptable salts, solvates, stereoisomers, tautomers, and prodrugs of such compounds.

For compounds of Formula (I), substituent $R^1$ is selected from the group consisting of $(C_6$-$C_{14})$ heterocycloalkyl, $(C_6$-$C_{14})$ aryl, and $(C_6$-$C_{14})$ heteroaryl. When $R^1$ is phenyl, however, $R^1$ is substituted with one or more substituents selected from the group consisting of $(C_1$-$C_8)$alkyl, $(C_2$-$C_8)$alkenyl, $(C_2$-$C_8)$alkynyl, $(C_1$-$C_8)$alkoxy, aryl, heterocycle, $(C_1$-$C_8)$haloalkyl, —Cl, —Br, —I, —CN, —NO$_2$, heteroaryl, and $(C_1$-$C_6)$hydroxyalkyl.

Substituent $R^2$ is selected from the group consisting of halogen, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^3$ is selected from the group consisting of hydrogen, halogen, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^4$ is selected from the group consisting of halogen, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

For compounds of Formula (II), substituent $R^5$ is selected from the group consisting of $(C_6$-$C_{14})$ heterocycloalkyl, $(C_6$-$C_{14})$ aryl, and $(C_6$-$C_{14})$ heteroaryl. When $R^5$ is phenyl, however, $R^5$ is substituted with one or more substituents selected from the group consisting of $(C_1$-$C_8)$alkyl, $(C_2$-$C_8)$alkenyl, $(C_2$-$C_8)$alkynyl, $(C_1$-$C_8)$alkoxy, aryl, heterocycle, $(C_1$-$C_8)$haloalkyl, —Cl, —Br, —I, —CN, —NO$_2$, heteroaryl, and $(C_1$-$C_6)$hydroxyalkyl.

Substituent $R^6$ is selected from the group consisting of halogen, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^7$ is selected from the group consisting of hydrogen, halogen, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

For compounds of Formula (III), Substituent $R^{18}$ is selected from the group consisting of phenyl and monocyclic 6- to 14-membered heterocycloalkyl. When $R^{18}$ is phenyl, $R^8$ is substituted with one or more substituents selected from the group consisting of $(C_5$-$C_8)$alkyl, $(C_2$-$C_8)$alkenyl, $(C_2$-$C_8)$alkynyl, aryl, heterocycle, $(C_2$-$C_8)$haloalkyl, —NO$_2$, SF$_5$, heteroaryl, and $(C_1$-$C_6)$hydroxyalkyl.

Substituent $R^{19}$ is independently selected from the group consisting of —F, —Br, —I, —CN, —NO$_2$, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^{20}$ is independently selected from the group consisting of hydrogen, —F, —Br, —I, —CN, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^{21}$ is selected from the group consisting of hydrogen, halogen, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

For compounds of Formula (V), substituent $R^8$ is selected from the group consisting of bi- or tricyclic aryl, bi- or tricyclic heteroaryl, and unsaturated bi- or tricyclic cycloalkyl or heterocycloalkyl.

Substituent $R^9$ is independently selected from the group consisting of hydrogen, —F, —Br, —I, $(C_1$-$C_8)$alkyl, $(C_2$-$C_8)$alkenyl, $(C_2$-$C_8)$alkynyl, and $(C_1$-$C_8)$haloalkyl.

Substituent $R^{10}$ is independently selected from the group consisting of hydrogen, halogen, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^{11}$ is selected from the group consisting of hydrogen, halogen, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^{12}$ is selected from the group consisting of hydrogen, $(C_1$-$C_8)$alkyl, $(C_2$-$C_8)$alkenyl, $(C_2$-$C_8)$alkynyl, $(C_1$-$C_8)$alkoxy, aryl, heterocycle, $(C_1$-$C_8)$haloalkyl, halogen, —CN, —NO$_2$, hydroxyl, heteroaryl, and $(C_1$-$C_6)$hydroxyalkyl.

For compounds of Formula (VI), substituent $R^{13}$ is selected from the group consisting of $(C_3$-$C_{14})$cycloalkyl, 3- to 14-membered heterocycloalkyl, bi- or tri-cyclic aryl, and 5- to 10-membered heteroaryl.

Substituent $R^{14}$ is independently selected from the group consisting of hydrogen, —F, —Br, —I, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^{15}$ is independently selected from the group consisting of hydrogen, halogen, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^{16}$ is selected from the group consisting of hydrogen, halogen, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^{17}$ is selected from the group consisting of hydrogen, $(C_1$-$C_8)$alkyl, $(C_2$-$C_8)$alkenyl, $(C_2$-$C_8)$alkynyl, $(C_1$-$C_8)$alkoxy, aryl, heterocycle, $(C_1$-$C_8)$haloalkyl, halogen, —CN, —NO$_2$, hydroxyl, heteroaryl, and $(C_1$-$C_6)$hydroxyalkyl.

For compounds of Formula (VII), substituent $R^{26}$ is selected from the group consisting of substituted phenyl, optionally substituted 6- to 14-membered heterocycloalkyl, and 6- to 14-membered heteroaryl. When $R^{26}$ is phenyl and is mono-substituted, $R^{26}$ is substituted with a member selected from the group consisting of CN, NO$_2$, —NR$^a$R$^b$, $(C_2$-$C_8)$haloalkyl, $(C_1$-$C_8)$haloalkoxy, $(C_2$-$C_8)$alkoxy, aryloxy, $(C_5$-$C_8)$alkyl, $(C_1$-$C_8)$-alkylaryl, $(C_2$-$C_8)$alkene, $(C_2$-$C_8)$alkyne, and aryl.

Alternatively, when $R^{26}$ is phenyl and is di-, tri-, tetra-, or penta-substituted, $R^{26}$ is substituted with two or more members selected from the group consisting of F, I, Br, Cl, CN, NO$_2$, —NR$^a$R$^b$, $(C_1$-$C_8)$haloalkyl, $(C_1$-$C_8)$haloalkoxy, $(C_1$-$C_8)$alkoxy, aryloxy, $(C_1$-$C_8)$alkyl, $(C_1$-$C_8)$-alkylaryl, $(C_2$-$C_8)$alkene, $(C_2$-$C_8)$alkyne, $(C_1$-$C_8)$-alkylaryl, and aryl.

In embodiments where $R^{26}$ is a heterocycloalkyl or a heteroaryl, it is optionally substituted with one or more members selected from the group consisting of halogen, —CN, NO$_2$, oxo, hydroxyl, $(C_1$-$C_8)$alkyl, $(C_2$-$C_8)$alkenyl, $(C_2$-$C_8)$alkynyl, $(C_1$-$C_4)$alkoxy, $(C_1$-$C_4)$haloalkyl, and $(C_2$-$C_4)$hydroxyalkyl.

Substituent $R^{27}$ is selected from the group consisting of —F, —Br, —I, —CN, —NO$_2$, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^{28}$ is selected from the group consisting of hydrogen, —F, —Br, —I, —CN, $(C_1$-$C_8)$alkyl, $(C_2$-$C_8)$alkenyl, $(C_2$-$C_8)$alkynyl, $(C_1$-$C_8)$alkoxy, and $(C_1$-$C_8)$haloalkyl.

Substituent $R^{29}$ is selected from the group consisting of hydrogen, halogen, $(C_1-C_8)$alkyl, $(C_2-C_8)$alkenyl, $(C_2-C_8)$alkynyl, $(C_1-C_8)$alkoxy, and $(C_1-C_8)$haloalkyl.

In embodiments where $R^{26}$ is $NR^aR^b$, substituents $R^a$ and $R^b$ are each independently selected from the group consisting of H, $(C_1-C_8)$alkyl, aryl, heteroaryl, heterocycloalkyl, $(C_1-C_8)$haloalkoxy, $(C_1-C_8)$haloalkyl and $(C_1-C_6)$hydroxyalkyl.

Any heterocycloalkyl or heteroaryl defined herein is optionally substituted with one or more members selected from the group consisting of halogen, —CN, —NO$_2$, hydroxyl, $(C_1-C_8)$alkyl, $(C_2-C_8)$alkenyl, $(C_2-C_8)$alkynyl, $(C_1-C_4)$alkoxy, $(C_1-C_4)$haloalkyl, and $(C_2-C_4)$hydroxyalkyl.

The invention also provides pharmaceutical compositions of compounds that conform to Formula IV or Formula VIII, as well as pharmaceutically acceptable salts, solvates, stereoisomers, tautomers, and prodrugs of such compounds and a pharmaceutically acceptable carrier.

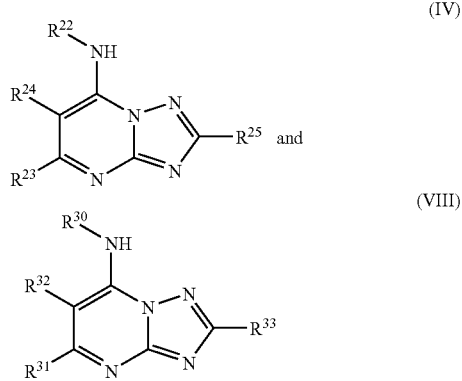

For compounds of Formula (IV), substituent $R^{22}$ is selected from the group consisting of phenyl and monocyclic 6- to 14-membered heterocycloalkyl. When $R^{22}$ is phenyl, $R^{22}$ is substituted with one or more substituents selected from the group consisting of $(C_1-C_8)$alkyl, $(C_2-C_8)$alkenyl, $(C_2-C_8)$alkynyl, aryl, heterocycle, $(C_1-C_8)$haloalkyl, —Cl, —NO$_2$, heteroaryl, and $(C_1-C_6)$hydroxyalkyl.

Substituent $R^{23}$ is independently selected from the group consisting of —F, —Br, —I, —CN, —NO$_2$, $(C_1-C_8)$alkyl, $(C_2-C_8)$alkenyl, $(C_2-C_8)$alkynyl, $(C_1-C_8)$alkoxy, and $(C_1-C_8)$haloalkyl.

Substituent $R^{24}$ is independently selected from the group consisting of hydrogen, —F, —Br, —I, —CN, $(C_1-C_8)$alkyl, $(C_2-C_8)$alkenyl, $(C_2-C_8)$alkynyl, $(C_1-C_8)$alkoxy, and $(C_1-C_8)$haloalkyl.

Substituent $R^{25}$ is selected from the group consisting of hydrogen, halogen, $(C_1-C_8)$alkyl, $(C_2-C_8)$alkenyl, $(C_2-C_8)$alkynyl, $(C_1-C_8)$alkoxy, and $(C_1-C_8)$haloalkyl.

For compounds of Formula (VIII), substituent $R^{30}$ is selected from the group consisting of substituted phenyl, optionally substituted 6- to 14-membered heterocycloalkyl, and 6- to 14-membered heteroaryl.

When $R^{30}$ is a phenyl, $R^{30}$ is substituted with one or more members selected from the group consisting of F, I, Br, Cl, CN, NO$_2$, —NR$^a$R$^b$, $(C_1-C_8)$haloalkyl, $(C_1-C_8)$haloalkoxy, $(C_1-C_8)$alkoxy, aryloxy, $(C_1-C_8)$alkyl, $(C_1-C_8)$-alkylaryl, $(C_2-C_8)$alkene, $(C_2-C_8)$alkyne, $(C_1-C_8)$-alkylaryl, and aryl.

In alternate embodiments, $R^{30}$ is a heterocycloalkyl or a heteroaryl. Accordingly, $R^{30}$ is optionally substituted with one or more members selected from the group consisting of halogen, —CN, NO$_2$, oxo, hydroxyl, $(C_1-C_8)$alkyl, $(C_2-C_8)$alkenyl, $(C_2-C_8)$alkynyl, $(C_1-C_4)$alkoxy, $(C_1-C_4)$haloalkyl, and $(C_2-C_4)$hydroxyalkyl.

Substituent $R^{31}$ is selected from the group consisting of —F, —Br, —I, —CN, —NO$_2$, $(C_1-C_8)$alkyl, $(C_2-C_8)$alkenyl, $(C_2-C_8)$alkynyl, $(C_1-C_8)$alkoxy, and $(C_1-C_8)$haloalkyl.

Substituent $R^{32}$ is selected from the group consisting of hydrogen, —F, —Br, —I, —CN, $(C_1-C_8)$alkyl, $(C_2-C_8)$alkenyl, $(C_2-C_8)$alkynyl, $(C_1-C_8)$alkoxy, and $(C_1-C_8)$haloalkyl.

Substituent $R^{33}$ is selected from the group consisting of hydrogen, halogen, $(C_1-C_8)$alkyl, $(C_2-C_8)$alkenyl, $(C_2-C_8)$alkynyl, $(C_1-C_8)$alkoxy, and $(C_1-C_8)$haloalkyl.

Any heterocycloalkyl or heteroaryl defined herein is optionally substituted with one or more members selected from the group consisting of halogen, —CN, —NO$_2$, hydroxyl, $(C_1-C_8)$alkyl, $(C_2-C_8)$alkenyl, $(C_2-C_8)$alkynyl, $(C_1-C_4)$alkoxy, $(C_1-C_4)$haloalkyl, and $(C_2-C_4)$hydroxyalkyl.

Another embodiment of the present invention relates to treating malaria by administering to a subject in need of such treatment a therapeutically effective amount of a compound as described above. The invention further contemplates inhibiting dihydroorotate dehydrogenase in a parasite by contacting the parasite with such a compound, e.g., by administering to a mammalian host of the parasite an effective amount of the compound. In this latter context, mammalian dihydroorotate dehydrogenase is not thereby inhibited. In one embodiment, the parasite is *Plasmodium falciparum*.

Another embodiment optionally in combination with any other embodiment described herein is a compound described herein for use in the manufacture of a medicament for the treatment of malaria. Another embodiment similarly is a compound described herein for use in the manufacture of a medicament for the or for the inhibition of dihydroorotate dehydrogenase in a parasite without inhibition of mammalian dihydroorotate dehydrogenase.

It should be understood that the following compounds are excluded from Formulae VII and VIII:
5-methyl-N-(quinolin-6-yl)-[1,2,4]triazolo-[1,5-a]pyrimidin-7-amine,
5-methyl-N-(quinolin-3-yl)-[1,2,4]triazolo-[1,5-a]pyrimidin-7-amine, and
5-methyl-N-(4H-chromen-4-on-7-yl)-[1,2,4]triazolo-[1,5-a]pyrimidin-7-amine.

These and other embodiments of this invention will be evident by reference to the following detailed description. To that end, certain patent and other documents are cited here, to set forth various embodiments of the invention more specifically.

FIGURES

FIG. 1A depicts plasma concentrations after a single oral dose (20 mg/kg or 50 mg/kg) in mice.

FIG. 1B shows efficacy in the standard *P. berghei* mouse model. Dosing was b.i.d. 50 mg/kg. Arrows indicate the dosing times.

DETAILED DESCRIPTION OF THE INVENTION

Definitions

The term "alkyl" refers to a straight or branched chain, saturated hydrocarbon having the indicated number of carbon atoms. For example, $(C_1-C_8)$alkyl is meant to include but is not limited to methyl, ethyl, propyl, isopropyl, butyl, sec-butyl, tert-butyl, pentyl, isopentyl, neopentyl, hexyl, isohexyl, and neohexyl, etc. An alkyl group can be unsubstituted or optionally substituted with one or more substituents as described herein below.

The term "alkenyl" refers to a straight or branched chain unsaturated hydrocarbon having the indicated number of carbon atoms and at least one double bond. Examples of a ($C_2$-$C_8$)alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term "alkynyl" refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkoxy" refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aryl" refers to a 6- to 18-membered bicyclic, tricyclic, or polycyclic aromatic hydrocarbon ring system. Examples of an aryl group include naphthyl, pyrenyl, and anthracyl. An aryl group can be unsubstituted or optionally substituted with one or more substituents as described herein below.

The term "halogen" and "halo" refers to —F, —Cl, —Br or —I.

The term "heteroatom" is meant to include oxygen (O), nitrogen (N), and sulfur (S).

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "cycloalkyl" refer to monocyclic, bicyclic, tricyclic, or polycyclic, 3- to 14-membered ring systems, which are either saturated, unsaturated or aromatic. The heterocycle may be attached via any heteroatom or carbon atom. Cycloalkyl include aryls and hetroaryls as defined above. Representative examples of cycloalkyl include, but are not limited to, cycloethyl, cyclopropyl, cycloisopropyl, cyclobutyl, cyclopentyl, cyclohexyl, cyclopropene, cyclobutene, cyclopentene, cyclohexene, phenyl, naphthyl, anthracyl, benzofuranyl, and benzothiophenyl. A cycloalkyl group can be unsubstituted or optionally substituted with one or more substituents as described herein below.

The term "nitrile or cyano" can be used interchangeably and refer to a —CN group which is bound to a carbon atom of a heteroaryl ring, aryl ring and a heterocycloalkyl ring.

The term "amine or amino" refers to an —$NR^aR^b$ group wherein $R^a$ and $R^b$ each independently refer to a hydrogen, ($C_1$-$C_8$)alkyl, aryl, heteroaryl, heterocycloalkyl, ($C_1$-$C_8$)haloalkyl, and ($C_1$-$C_6$)hydroxyalkyl group.

The term "aryloxy" refers to an —O-aryl group having the indicated number of carbon atoms. Examples of aryloxy groups include, but are not limited to, phenoxy, napthoxy and cyclopropeneoxy.

The term "haloalkoxy," refers to an —O—($C_1$-$C_8$)alkyl group wherein one or more hydrogen atoms in the $C_1$-$C_8$ alkyl group is replaced with a halogen atom, which can be the same or different. Examples of haloalkyl groups include, but are not limited to, difluoromethocy, trifluoromethoxy, 2,2,2-trifluoroethoxy, 4-chlorobutoxy, 3-bromopropyloxy, pentachloroethoxy, and 1,1,1-trifluoro-2-bromo-2-chloroethoxy.

The term "alkylaryl" refers to $C_1$-$C_8$ alkyl group in which at least one hydrogen atom of the $C_1$-$C_8$ alkyl chain is replaced by an aryl atom, which may be optionally substituted with one or more substituents as described herein below. Examples of alkylaryl groups include, but are not limited to, methylphenyl, ethylnaphthyl, propylphenyl, and butylphenyl groups.

The term "oxo" refers to a =O atom attached to a saturated or unsaturated ($C_3$-$C_8$) cyclic or a ($C_1$-$C_8$) acyclic moiety. The =O atom can be attached to a carbon, sulfur, and nitrogen atom that is part of the cyclic or acyclic moiety. Exemplary of oxo compounds, but not limited to are chromene-4-one, and 2-nitrosoethylbenzene.

The terms "heterocycle" and "heterocycloalkyl" refer to bicyclic, tricyclic, or polycyclic systems, which are either unsaturated or aromatic and which contains from 1 to 4 heteroatoms, independently selected from nitrogen, oxygen and sulfur, wherein the nitrogen and sulfur heteroatoms are optionally oxidized and the nitrogen heteroatom optionally quaternized, including bicyclic, and tricyclic ring systems. The bicyclic or tricyclic ring systems may be spiro-fused. The bicyclic and tricyclic ring systems may encompass a heterocycle or heteroaryl fused to a benzene ring. The heterocycle may be attached via any heteroatom or carbon atom. Heterocycles include heteroaryls as defined above. Representative examples of heterocycles include, but are not limited to, benzoxazolyl, benzisoxazolyl, benzthiazolyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below. According to Formulae III to VIII, the cyclic systems further comprises one or more monocyclic systems. According to Formulae I and II, the cyclic systems may comprise one or more 8- to 14-membered ring systems. According to Formulae III-VI, the cyclic systems may comprise one or more 3- to 14-membered ring systems. According to Formulae VII and VIII, the cyclic systems may comprise one or more 6- to 14-membered ring systems.

According to Formulae I-VI, the term "haloalkyl," refers to a $C_1$-$C_6$ alkyl group wherein one or more hydrogen atoms in the $C_1$-$C_6$ alkyl group is replaced with a halogen atom, which can be the same or different. According to Formulae VII-VIII, the term "haloalkyl," refers to a $C_1$-$C_8$ alkyl group wherein one or more hydrogen atoms in the $C_1$-$C_8$ alkyl group is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

According to Formulae I and II, the term "heteroaryl" denotes a polycyclic aromatic heterocyclic ring system ring of 5 to 18 members, having at least one heteroatom selected from nitrogen, oxygen and sulfur, and containing at least 1 carbon atom, including bicyclic, and tricyclic ring systems.

According to Formulae III-VI, the term "heteroaryl" denotes a aromatic heterocyclic 5- to 10-membered ring system, having at least one heteroatom selected from nitrogen, oxygen and sulfur, and containing at least 1 carbon atom, including monocyclic, bicyclic, and tricyclic ring systems. According to Formulae VII and VIII, the term "heteroaryl" denotes a aromatic heterocyclic 6- to 14-membered ring system, having at least one heteroatom selected from nitrogen, oxygen and sulfur, and containing at least 1 carbon atom, including monocyclic, bicyclic, and tricyclic ring systems. Examples of heteroaryls are benzofuranyl, benzothiophenyl, quinolinyl, indolyl, benzoxazolyl, benzimidazolyl, benzothiazolyl, pyrimidinyl, cinnolinyl, phthalazinyl, quinazolinyl, pyrimidyl, chromenonyl, quinoxalinyl. A heteroaryl group can be unsubstituted or optionally substituted with one or more substituents as described herein below. The heteroaryl group in some embodiments is monocyclic with one or more substituents.

Substituents for the groups referred to as alkyl, heteroalkyl, alkylene, alkenyl, and alkynyl can be a variety of groups selected from: —OR', =O, =NR', =N—OR', —NR'R", —SR', —halo, —SiR'R"R'", —OC(O)R', —C(O)R', —CO$_2$R', —CONR'R", —OC(O)NR'R", —NR"C(O)R', —NR'"C(O)NR'R", —NR'"SO$_2$NR'R", —NR"CO$_2$R', —NHC(NH$_2$)=NH, —NR'C(NH$_2$)=NH, —NHC(NH$_2$)=NR', —S(O)R', —SO$_2$R', —SO$_2$NR'R", —NR"SO$_2$R', —CN and —NO$_2$, in a number ranging from zero to three, with those groups having zero, one or two substituents being exemplary. R', R" and R'" each independently refer to hydrogen, unsubstituted (C$_1$-C$_8$)alkyl, unsubstituted hetero(C$_1$-C$_8$)alkyl, unsubstituted aryl and aryl substituted with one to three substituents selected from -halo, unsubstituted alkyl, unsubstituted alkoxy, unsubstituted thioalkoxy and unsubstituted aryl(C$_1$-C$_4$)alkyl. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. An alkyl or heteroalkyl group will have from zero to three substituents, with those groups having two or fewer substituents being exemplary in the present invention. In some embodiments, an alkyl or heteroalkyl radical will be unsubstituted or monosubstituted. An alkyl or heteroalkyl radical can be unsubstituted. From the above discussion of substituents, one of skill in the art will understand that the term "alkyl" is meant to include groups such as trihaloalkyl (e.g., —CF$_3$ and —CH$_2$CF$_3$).

Exemplary substituents for the alkyl and heteroalkyl radicals are selected from: —OR', =O, —NR'R", —SR', -halo, —SiR'R"R'", —OC(O)R', —C(O)R', —CO$_2$R', —C(O)NR'R", —OC(O)NR'R", —NR"C(O)R', —NR"CO$_2$R', —NR'"SO$_2$NR'R", —S(O)R', —SO$_2$R', —SO$_2$NR'R", —NR"SO$_2$R', —CN and —NO$_2$, where R', R" and R'" are as defined above. Typically, substituents are selected from: —OR', =O, —NR'R", -halo, —OC(O)R', —CO$_2$R', —C(O)NR'R", —OC(O)NR'R", —NR"C(O)R', —NR"CO$_2$R', —NR'"SO$_2$NR'R", —SO$_2$R', —SO$_2$NR'R", —NR"SO$_2$R'—CN and —NO$_2$.

Similarly, substituents for the aryl and heteroaryl groups are varied and selected from: -halo, —OR', —OC(O)R', —NR'R", —SR', —R', —CN, —NO$_2$, —CO$_2$R', —C(O)NR'R", —C(O)R', —OC(O)NR'R", —NR"C(O)R', —NR"CO$_2$R', —NR'"C(O)NR'R", —NR'"SO$_2$NR'R", —NHC(NH$_2$)=NH, —NR'C(NH$_2$)=NH, —NH—C(NH$_2$)=NR', —S(O)R', —SO$_2$R', —SO$_2$NR'R", —NR"SO$_2$R', —N$_3$, —CH(Ph)$_2$, perfluoroalkoxy and perfluoro(C$_1$-C$_4$)alkyl, in a number ranging from zero to the total number of open valences on the aromatic ring system; and where R', R" and R'" are independently selected from hydrogen, unsubstituted (C$_1$-C$_8$)alkyl, unsubstituted hetero(C$_1$-C$_8$)alkyl, unsubstituted aryl, unsubstituted heteroaryl, unsubstituted aryl(C$_1$-C$_4$)alkyl and unsubstituted aryloxy(C$_1$-C$_4$)alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Exemplary substituents for aryl and heteroaryl groups are selected from: -halo, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R', —N$_3$, —CH(Ph)$_2$, perfluoroalkoxy and perfluoro(C$_1$-C$_4$)alkyl, where R' and R" are as defined above.

Typically, substituents are selected from: -halo, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R', perfluoroalkoxy and perfluoro(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R$^1$ in —NR'— and —S(O)$_2$NR'— is selected from hydrogen or unsubstituted (C$_1$-C$_6$)alkyl.

The substituent —CO$_2$H, may be replaced with bioisosteric replacements such as:

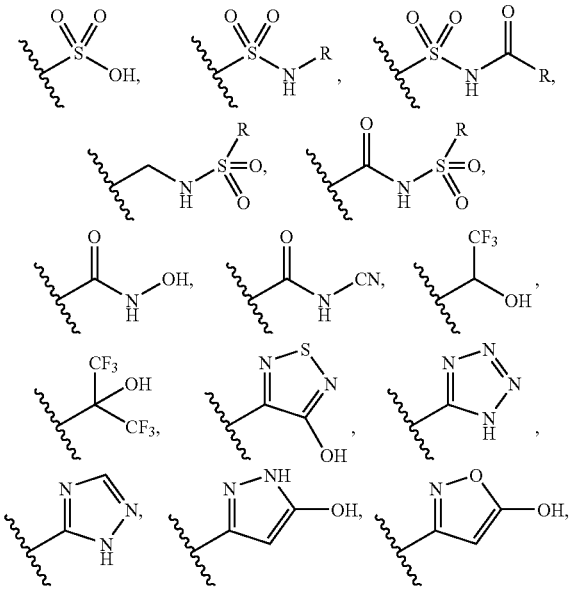

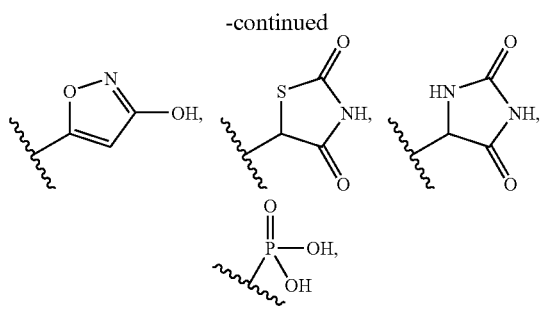

and the like. See, e.g., THE PRACTICE OF MEDICINAL CHEMISTRY (Academic Press: New York, 1996), at page 203.

The compound of the invention can also exist in various isomeric forms, including configurational, geometric, and conformational isomers, as well as existing in various tautomeric forms, particularly those that differ in the point of attachment of a hydrogen atom. The term "isomer" is intended to encompass all isomeric forms of a compound of this invention, including tautomeric forms of the compound.

Certain compounds described here may have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

In this description, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The term "prodrug" denotes a derivative of a compound that can hydrolyze, oxidize, or otherwise react under biological conditions, in vitro or in vivo, to provide an active compound, particularly a compound of the invention. Examples of prodrugs include, but are not limited to, derivatives and metabolites of a compound of the invention that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). For instance, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by BURGER'S MEDICINAL CHEMISTRY AND DRUG DISCOVERY $6^{th}$ ed. (Wiley, 2001) and DESIGN AND APPLICATION OF PRODRUGS (Harwood Academic Publishers Gmbh, 1985).

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound of the invention or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

The terms "modulate", "modulation" and the like refer to the ability of a compound to increase or decrease the function, or activity of, for example, DHODH. "Modulation", in its various forms, is intended to encompass inhibition, antagonism, partial antagonism, activation, agonism and/or partial agonism of the activity associated with DHODH. DHODH inhibitors are compounds that, e.g., bind to, partially or totally block stimulation, decrease, prevent, delay activation, inactivate, desensitize, or down regulate signal transduction. DHODH activators are compounds that, e.g., bind to, stimulate, increase, open, activate, facilitate, enhance activation, sensitize or up regulate signal transduction. The ability of a compound to modulate DHODH can be demonstrated in an enzymatic assay or a cell-based assay.

A "patient" includes an animal (e.g., cow, horse, sheep, pig, chicken, turkey, quail, cat, dog, mouse, rat, rabbit or guinea pig), in one embodiment a mammal such as a non-primate and a primate (e.g., monkey and human), and in another embodiment a human. In one embodiment, a patient is a human. In specific embodiments, the patient is a human infant, child, adolescent or adult.

Compounds and Methods of the Invention

As noted above, the present invention relates to a compound according to Formula I, Formula II, Formula III, Formula V, Formula VI, or Formula VII,

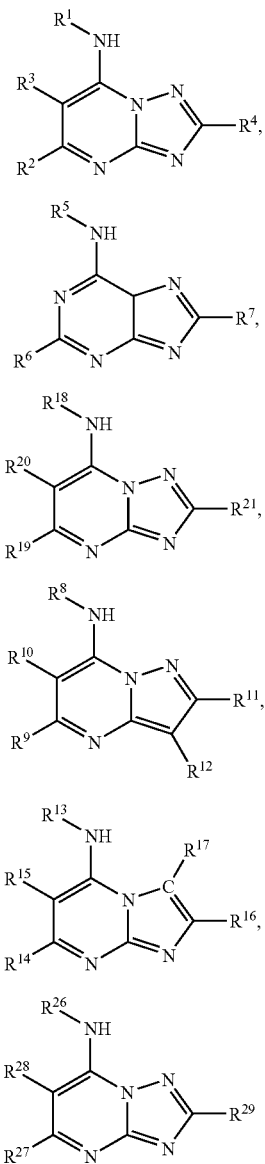

and to a pharmaceutically acceptable salt, solvate, tautomer, stereoisomer, and prodrug, respectively, wherein all the variables are defined as above.

Another embodiment of this present invention relates to a pharmaceutical composition comprising a compound according to Formula IV or Formula VIII:

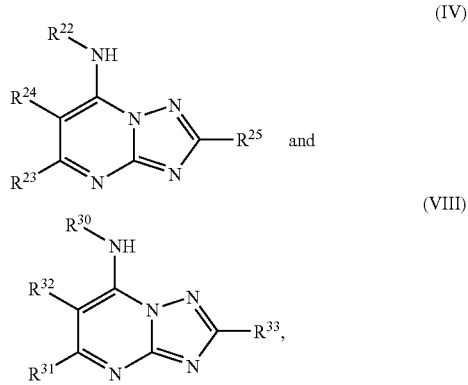

and to a pharmaceutically acceptable salt, solvate, tautomer, stereoisomer, and prodrug, respectively, wherein all the variables are defined as above.

In one embodiment, the compound is one according to Formula (I)

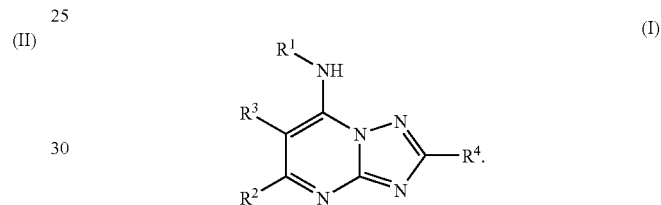

In one embodiment, $R^4$ is $(C_1-C_3)$alkyl. For instance, $R^4$ can be methyl.

In one embodiment, $R^3$ is selected from a group consisting of hydrogen, halogen, and $(C_1-C_3)$ alkyl. For example, in one embodiment, $R_3$ is Cl. In another embodiment $R_3$ is H. In still further embodiments, $R_3$ is methyl.

In one embodiment, $R^2$ and $R^3$ are independently $(C_1-C_3)$ alkyl. In another embodiment, $R^2$ is methyl and $R^3$ is hydrogen. In another embodiment, $R^2$ and $R^4$ is methyl.

In one embodiment, $R^1$ is $(C_6-C_{14})$heterocycloalkyl. In other embodiments, $R^1$ is $(C_6-C_{14})$aryl. Yet in other embodiments, $R^1$ is $(C_6-C_{14})$heteroaryl.

In still further embodiments, $R^1$ is phenyl. In these instances, the phenyl group is substituted with one or more substituents selected from the group consisting of $(C_1-C_8)$ alkyl, $(C_2-C_8)$alkenyl, $(C_2-C_8)$alkynyl, $(C_1-C_8)$alkoxy, aryl, heterocycle, $(C_1-C_8)$haloalkyl, —Cl, —Br, —I, —CN, —NO$_2$, heteroaryl, and $(C_1-C_6)$hydroxyalkyl. In one embodiment, $R^1$ is $(C_1-C_4)$ haloalkyl substituted phenyl, for example, CF$_3$ substituted phenyl.

Another of the invention provide a compound according to Formula (II)

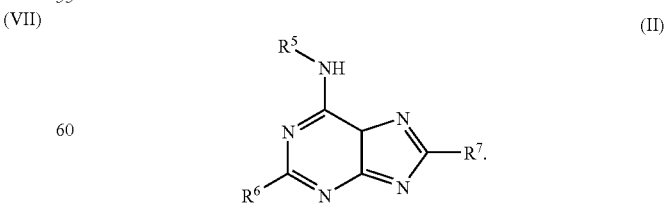

In one embodiment, $R^7$ is hydrogen.
In one embodiment, $R^5$ is phenyl that is substituted with one or more substituents selected from the group consisting of $(C_1-C_8)$alkyl, $(C_2-C_8)$alkenyl, $(C_2-C_8)$alkynyl, $(C_1-C_8)$ alkoxy, aryl, heterocycle, $(C_1-C_8)$haloalkyl, —Cl, —Br, —I, —CN, —NO$_2$, heteroaryl, and $(C_1-C_6)$hydroxyalkyl.

In one embodiment, $R^5$ is $(C_6-C_{14})$heteroaryl. Alternatively, $R^5$ is $(C_6-C_{14})$heterocycloaryl or $(C_6-C_{14})$heterocycloalkyl.

In one embodiment, $R^6$ is $(C_1-C_3)$alkyl. For example, $R^6$ can be methyl. In some embodiments, $R^6$ is methyl and $R^7$ is hydrogen.

Exemplary compounds according to the invention include but are not limited to 2-methyl-N-(naphthalen-2-yl)-9H-purin-6-amine, 2,5-Dimethyl-[1,2,4]triazolo[1,5-a]pyrimidin-7-yl)-naphthalen-2-yl-amine, 2,5-Dimethyl-[1,2,4]triazolo[1,5-a]pyrimidin-7-yl)-anthracen-2-yl-amine, 2-ethyl-5-methyl-N-(4-(trifluoromethyl)phenyl)-[1,2,4]triazolo[1,5-a]pyrimidin-7-amine, 5-methyl-2-(thiazol-5-yl)-N-(4-(trifluoromethyl)phenyl)-[1,2,4]triazolo[1,5-a]pyrimidin-7-amine, 2-methoxy-5-methyl-N-(4-(trifluoromethyl)phenyl)-[1,2,4]triazolo[1,5-a]pyrimidin-7-amine, 2-ethoxy-5-methyl-N-(4-(trifluoromethyl)phenyl)-[1,2,4]triazolo[1,5-a]pyrimidin-7-amine, 5-methyl-2-propoxy-N-(4-(trifluoromethyl)phenyl)-[1,2,4]triazolo[1,5-a]pyrimidin-7-amine, 2-ethynyl-5-methyl-N-(4-(trifluoromethyl)phenyl)-[1,2,4]triazolo[1,5-a]pyrimidin-7-amine, 5-methyl-7-(4-(trifluoromethyl)phenylamino)-[1,2,4]triazolo[1,5-a]pyrimidine-2-carboxamide, 2-(2-(dimethylamino)ethoxy)-5-methyl-N-(4-(trifluoromethyl)phenyl)-[1,2,4]triazolo[1,5-a]pyrimidin-7-amine, 2,5-dimethyl-N-(4-(trifluoromethyl)phenyl)-[1,2,4]triazolo[1,5-a]pyrimidin-7-amine, 6-chloro-2,5-dimethyl-N-(4-(trifluoromethyl)phenyl)-[1,2,4]triazolo[1,5-a]pyrimidin-7-amine, and 2,5,6-trimethyl-N-(4-(trifluoromethyl)phenyl)-[1,2,4]triazolo[1,5-a]pyrimidin-7-amine.

The compounds according to the invention also include compounds according to Formula I-a:

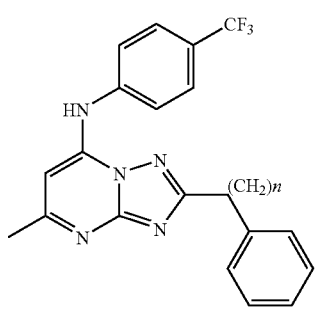

(I-a)

wherein n is an integer selected from 1 to 8, and pharmaceutically acceptable salts, solvates, stereoisomers, tautomers, and prodrugs thereof. For example, the compound is 2-(5-methyl-7-(4-(trifluoromethyl)phenylamino)-[1,2,4]triazolo[1,5-a]pyrimidin-2-yl)acetamide or 2-benzyl-5-methyl-N-(4-(trifluoromethyl)phenyl)-[1,2,4]triazolo[1,5-a]pyrimidin-7-amine.

In one embodiment, the compound is one according to Formula III

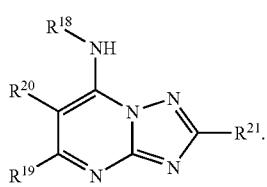

(III)

In one embodiment, $R^{18}$ is phenyl.
In another embodiment, $R^{20}$ is hydrogen.
In still further embodiments, $R^{21}$ is hydrogen.

In one embodiment, $R^{19}$ is $(C_1-C_3)$alkyl. For instance, $R^{19}$ is methyl.

In one embodiment, the pharmaceutical composition is one according to Formula IV:

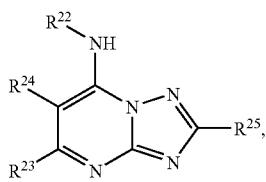

(IV)

In one embodiment, $R^{22}$ is phenyl. When $R^{22}$ is phenyl, $R^{22}$ can be substituted with one or more substituents selected from the group consisting of $(C_1-C_8)$alkyl, $(C_2-C_8)$alkenyl, $(C_2-C_8)$alkynyl, aryl, heterocycle, $(C_1-C_8)$haloalkyl, —Cl, —NO$_2$, heteroaryl, and $(C_1-C_6)$hydroxyalkyl. For instance, $R^{22}$ is $(C_1-C_4)$haloalkyl substituted phenyl, for example, $R^{22}$ is substituted by —CF$_3$. For instance, $R^{22}$ is substituted by —Cl.

In one embodiment, $R^{24}$ is $(C_1-C_3)$ alkyl. For instance, $R^{24}$ is methyl. In another embodiment, $R^{24}$ is hydrogen.

In still further embodiments, $R^{25}$ is hydrogen.
In one embodiment, $R^{23}$ is $(C_1-C_3)$alkyl. For instance, $R^{23}$ is methyl.

Exemplary compounds according to the invention include but are not limited to 5-Methyl-[1,2,4]triazolo[1,5-a]pyrimidin-7-yl)-(4-trifluoromethyl-phenyl)-amine and 5-Methyl-[1,2,4]triazolo[1,5-a]pyrimidin-7-yl)-(3-chloro-phenyl)-amine, and pharmaceutically acceptable salts, solvates, stereoisomers, tautomers, and prodrugs thereof.

In one embodiment, the compound is one according to Formula V

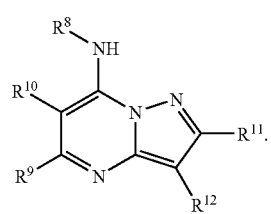

(V)

In one embodiment, $R^8$ is naphthyl.
In another embodiment, $R^{11}$ is hydrogen.
In still further embodiments, $R^9$ is $(C_1-C_3)$alkyl. For instance, $R^9$ can be methyl.
In one embodiment, $R^{10}$ is hydrogen.
In one embodiment, the compound is one according to Formula VI:

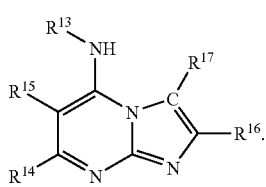

(VI)

In one embodiment, $R^{13}$ is naphthyl.
In another embodiment, $R^{15}$ is hydrogen.
In still further embodiments, $R^{14}$ is $(C_1-C_3)$alkyl. For instance, $R^{14}$ can be methyl.
In one embodiment, $R^{16}$ is hydrogen.

Exemplary compounds according to Formula III or Formula IV include but are not limited to 5-Methyl-pyrazolo[1,5-a]pyrimidin-7-yl)-naphthalen-2-yl-amine and 7-Methyl-imidazo[1,2-a]pyrimidin-5-yl)-naphthalen-2-yl-amine, 5,6-dimethyl-N-(4-(trifluoromethyl)phenyl)-[1,2,4]triazolo[1,5-a]pyrimidin-7-amine, and pharmaceutically acceptable salts, solvates, stereoisomers, tautomers, and prodrugs thereof.

In some embodiments, compounds of this invention may include but not limited to compounds according to Formula IV-a:

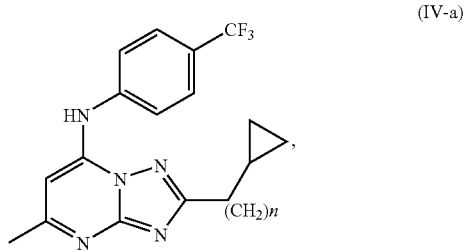 [SMILES: Cc1cc(Nc2ccc(C(F)(F)F)cc2)n2nc(CC3CC3)nc2n1]

(IV-a)

wherein n is an integral selected from 1 to 8, for example, in one embodiment, the compound is 2-(cyclopropylmethyl)-5-methyl-N-(4-(trifluoromethyl)phenyl)-[1,2,4]triazolo[1,5-a]pyrimidin-7-amine.

For compounds that conform to Formula VII, $R^{26}$ can be a substituted phenyl, optionally substituted 6- to 14-membered heterocycloalkyl, and 6- to 14-membered heteroaryl. When $R^{26}$ is a substituted phenyl, it may be mono-substituted with CN, $NO_2$, $-NR^aR^b$, $(C_2-C_8)$haloalkyl, $(C_1-C_8)$haloalkoxy, $(C_2-C_8)$alkoxy, aryloxy, $(C_5-C_8)$alkyl, $(C_1-C_8)$-alkylaryl, $(C_2-C_8)$alkene, $(C_2-C_8)$alkyne, and aryl. For mono-substituted phenyl analogs the alkyl, alkyne, and dimethyl amino groups are potent inhibitors of the *plasmodium falciparum* enzyme dihydroorotate dehydrogenase.

Alternatively, $R^{26}$ is di-, tri-, tetra- and penta-substituted phenyl group. For instance, $R^{26}$ can be substituted with F, Cl, Br, CN, methyl and trifluoromethyl group. Within this class of compounds, typical compounds in which the phenyl group is di-substituted, such as the trifluoromethyl-halogen, trifluoromethyl-methyl and dimethyl analogs have been found to be potent inhibitors of the *plasmodium falciparum* enzyme dihydroorotate dehydrogenase (pfDHODH).

In one embodiment, $R^{28}$ and $R^{29}$ are hydrogen and $R^{27}$ is $(C_1-C_3)$alkyl. For instance, $R^{27}$ is methyl.

In pharmaceutical compositions of compounds depicted by Formula VIII, $R^{30}$ can be a substituted phenyl, optionally substituted 6- to 14-membered heterocycloalkyl, and 6- to 14-membered heteroaryl. When $R^{30}$ is a substituted phenyl, it may be mono-, di-, tri-, tetra- and penta-substituted phenyl group. For instance, $R^{30}$ can be substituted with one or more substituents selected from $(C_1-C_8)$haloalkyl, $(C_1-C_8)$haloalkoxy, $(C_1-C_8)$alkoxy, aryloxy, $(C_1-C_8)$alkyl, $(C_1-C_8)$ alkylaryl, $(C_2-C_8)$alkene, $(C_2-C_8)$alkyne, $(C_1-C_8)$-alkylaryl, and aryl, F, Cl, Br, CN, methyl and trifluoromethyl group. Examples of phenyl substituted compounds that have potent inhibitory activity are those in which $R^{30}$ is a trifluoromethyl, trifluoromethoxy, and alkyl substituents.

In another embodiment, $R^{32}$ and $R^{33}$ are hydrogen and $R^{31}$ is $(C_1-C_3)$alkyl. For instance, $R^{31}$ is methyl.

Several potent inhibitors of pfDHODH include a 6- to 14-membered heterocycloalkyl or heteroaryl group for $R^{26}$ in Formula VII or $R^{30}$ in Formula VIII. Examples of such groups include, but are not limited to optionally substituted chroman-4-one, quinoline, indole and benzothiazole groups.

It should be understood that the following compounds are excluded from formulae VII and VIII:

5-methyl-N-(quinolin-6-yl)-[1,2,4]triazolo-[1,5-a]pyrimidin-7-amine, 5-methyl-N-(quinolin-3-yl)-[1,2,4]triazolo-[1,5-a]pyrimidin-7-amine, and 5-methyl-N-(4H-chromen-4-on-7-yl)-[1,2,4]triazolo-[1,5-a] pyrimidin-7-amine.

Pharmaceutical Compositions and Dosage

The invention encompasses a pharmaceutical composition comprising, with a pharmaceutically acceptable carrier, a compound according to Formulae I-VIII, or a pharmaceutically acceptable salt, solvate, stereoisomer, tautomer, or prodrug thereof. The composition may contain one or more additional therapeutic agents, such as a pyrimidine biosynthesis inhibitor, for example.

In one embodiment, the pharmaceutical composition comprises a compound selected from the group comprising of 2-methyl-N-(naphthalen-2-yl)-9H-purin-6-amine, 2,5-Dimethyl-[1,2,4]triazolo[1,5-o]pyrimidin-7-yl)-naphthalen-2-yl-amine, 2,5-Dimethyl-[1,2,4]triazolo[1,5-x]pyrimidin-7-yl)-anthracen-2-yl-amine, 5-Methyl-[1,2,4]triazolo[1,5-a] pyrimidin-7-yl)-(4-trifluoromethyl-phenyl)-amine and 5-Methyl-[1,2,4]triazolo[1,5-a]pyrimidin-7-yl)-(3-chloro-phenyl)-amine, 5-Methyl-pyrazolo[1,5-a]pyrimidin-7-yl)-naphthalen-2-yl-amine and 7-Methyl-imidazo[1,2-a]pyrimidin-5-yl)-naphthalen-2-yl-amine, 2-ethyl-5-methyl-N-(4-(trifluoromethyl)phenyl)-[1,2,4]triazolo[1,5-a]pyrimidin-7-amine, 5-methyl-2-(thiazol-5-yl)-N-(4-(trifluoromethyl)phenyl)-[1,2,4]triazolo[1,5-a]pyrimidin-7-amine, 2-methoxy-5-methyl-N-(4-(trifluoromethyl)phenyl)-[1,2,4]triazolo[1,5-a]pyrimidin-7-amine, 2-ethoxy-5-methyl-N-(4-(trifluoromethyl)phenyl)-[1,2,4]triazolo[1,5-a]pyrimidin-7-amine, 5-methyl-2-propoxy-N-(4-(trifluoromethyl)phenyl)-[1,2,4]triazolo[1,5-a]pyrimidin-7-amine, 2-ethynyl-5-methyl-N-(4-(trifluoromethyl)phenyl)-[1,2,4]triazolo[1,5-a]pyrimidin-7-amine, 5-methyl-7-(4-(trifluoromethyl)phenylamino)-[1,2,4]triazolo[1,5-a]pyrimidine-2-carboxamide, 2-(2-(dimethylamino)ethoxy)-5-methyl-N-(4-(trifluoromethyl)phenyl)-[1,2,4]triazolo[1,5-a]pyrimidin-7-amine, 2,5-dimethyl-N-(4-(trifluoromethyl)phenyl)-[1,2,4]triazolo[1,5-a]pyrimidin-7-amine, 6-chloro-2,5-dimethyl-N-(4-(trifluoromethyl)phenyl)-[1,2,4]triazolo[1,5-a]pyrimidin-7-amine, or 2,5,6-trimethyl-N-(4-(trifluoromethyl)phenyl)-[1,2,4]triazolo[1,5-a]pyrimidin-7-amine, 2-(5-methyl-7-(4-(trifluoromethyl)phenylamino)-[1,2,4]triazolo[1,5-a]pyrimidin-2-yl)acetamide, 2-benzyl-5-methyl-N-(4-(trifluoromethyl)phenyl)-[1,2,4]triazolo[1,5-a]pyrimidin-7-amine, 5,6-dimethyl-N-(4-(trifluoromethyl)phenyl)-[1,2,4]triazolo[1,5-a]pyrimidin-7-amine, 2-(cyclopropylmethyl)-5-methyl-N-(4-(trifluoromethyl)phenyl)-[1,2,4]triazolo[1,5-a]pyrimidin-7-amine, or compounds listed in Table 4 and Table 5 below, or a pharmaceutically acceptable salt, solvate, stereoisomer, tautomer, or prodrug thereof, and a pharmaceutically acceptable carrier.

Pharmaceutical compositions and single unit dosage forms comprising a compound of the invention, or a pharmaceutically acceptable stereoisomer, prodrug, salt, solvate, hydrate, tautomer, or clathrate thereof, are also encompassed by the invention.

In accordance with this invention, the aforementioned compounds of the invention or their pharmaceutically acceptable salts are useful in pharmaceutically acceptable compositions. These pharmaceutical compositions of the invention contain said compound of the invention or its pharmaceutically acceptable salts, in association with a compatible pharmaceutically acceptable carrier material. Any conventional carrier material can be utilized. The carrier material can be an organic or inorganic inert carrier material, for example one that is suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may also contain other pharmaceutically active agents. Additional additives such as flavoring agents, preservatives, stabilizers, emulsifying agents, buffers and the like may be added in accordance with accepted practices of pharmaceutical compounding.

The pharmaceutical preparations can be made up in any conventional form including a solid form for oral administration such as tablets, capsules, pills, powders, granules, and the like. The pharmaceutical preparations may be sterilized and/or may contain adjuvants such as preservatives, stabilizers, wetting agents, emulsifiers, salts for varying the osmotic pressure and/or buffers.

The compounds of the invention can also be administered to a patient in accordance with the invention by topical (including transdermal, buccal or sublingual), or parenteral (including intraperitoneal, subcutaneous, intravenous, intradermal or intramuscular injection) routes. In one embodiment, the compounds are administered orally. An oral dosage form comprises tablets, capsules of hard or soft gelatin methylcellulose or of another suitable material easily dissolved in the digestive tract. The oral dosages contemplated in accordance with the present invention will vary in accordance with the needs of the individual patient as determined by the prescribing physician. For instance, a daily dosage of from about 1 mg to about 50 mg per kg of body weight, such as from about 5 mg to about 25 mg per kg of body weight of the patient may be utilized.

It is within the purview of the present invention to incorporate the therapeutically active substance enumerated herein in any desired mount for enteral administration within the oral unit dosage form. For enteral or oral administration, particularly suitable are tablets, dragees or capsules having talc and/or carbohydrate carrier binder or the like, the carrier could be lactose and/or corn starch and/or potato starch. A syrup, elixir or the like can be used where a sweetened vehicle is employed. Sustained release compositions can be formulated including those where the active component is protected with differentially degradable coatings, e.g., by microencapsulation, multiple coatings, etc. For example, preparations containing the active substance of the present invention can be formulated in such a manner that each dose forms contains from about 50 mg to about 1000 mg, or about 250 mg, with suitable therapeutically inert fillers and diluents.

For parenteral application, particularly suitable are solutions, preferably oily or aqueous solutions as well as suspensions, emulsions, or implants, including suppositories. Therapeutic compounds will be formulated in sterile form in multiple or single dose formats such as being dispersed in a fluid carrier such as sterile physiological saline or 5% saline dextrose solutions commonly used with injectables.

For topical applications, the compound(s) of the invention can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

The actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. The dosage for treatment typically depends on the route of administration, the age, weight and degree of malarial infection of the patient.

In general, compounds of the invention for treatment can be administered to a subject in dosages used in prior malaria therapies. See, for example, the Physicians' Desk Reference. For example, a suitable effective dose of one or more compounds of the invention will be in the range of from 0.01 to 100 milligrams per kilogram of body weight of recipient per day, preferably in the range of from 1 to 50 milligrams per kilogram body weight of recipient per day, more preferably in the range of 5 to 25 milligrams per kilogram body weight of recipient per day. The desired dose is suitably administered once daily, or several sub-doses, e.g. 2 to 5 sub-doses, are administered at appropriate intervals through the day, or other appropriate schedule.

Therapeutic Uses of the Pharmaceutical Compositions of Formulae I-VIII

In one aspect, the invention provides methods of treating or preventing a condition or disorder associated with inhibition of *Plasmodium* dihydroorotate dehydrogenase by administering to a patient having such a condition or disorder a therapeutically effective amount of a compound of the invention. In some embodiments, the conditions or disorders, including diseases of humans, can be treated with inhibitors of *Plasmodium* DHODH, such as *P. falciparum* dihydroorotate dehydrogenase (pfDHODH).

The invention provides methods of inhibiting dihydroororate dehydrogenase in a parasite, comprising contacting said parasite with a compound of the invention. In one embodiment, the parasite is a member of the *Plasmodium* genus. In another embodiment, the parasite is *Plasmodium falciparum*.

In another embodiment, the invention provides methods of treating or preventing malaria, inhibiting dihydroororate dehydrogenase in a parasite, such as *Plasmodium falciparum*, in vitro or in vivo, or killing a *Plasmodium falciparum* parasite. The methods generally entail administration of a compound selected from the group consisting of 2-methyl-N-(naphthalen-2-yl)-9H-purin-6-amine, 2,5-Dimethyl-[1,2,4]triazolo[1,5-a]pyrimidin-7-yl)-naphthalen-2-yl-amine, 2,5-Dimethyl-[1,2,4]triazolo[1,5-a]pyrimidin-7-yl)-anthracen-2-yl-amine, 5-Methyl-[1,2,4]triazolo[1,5-a]pyrimidin-7-yl)-(4-trifluoromethyl-phenyl)-amine and 5-Methyl-[1,2,4]triazolo[1,5-a]pyrimidin-7-yl)-(3-chloro-phenyl)-amine, 5-Methyl-pyrazolo[1,5-a]pyrimidin-7-yl)-naphthalen-2-yl-amine and 7-Methyl-imidazo[1,2-a]pyrimidin-5-yl)-naphthalen-2-yl-amine, 2-ethyl-5-methyl-N-(4-(trifluoromethyl)phenyl)-[1,2,4]triazolo[1,5-a]pyrimidin-7-amine, 5-methyl-2-(thiazol-5-yl)-N-(4-(trifluoromethyl)phenyl)-[1,2,4]triazolo[1,5-a]pyrimidin-7-amine, 2-methoxy-5-methyl-N-(4-(trifluoromethyl)phenyl)-[1,2,4]triazolo[1,5-a]pyrimidin-7-amine, 2-ethoxy-5-methyl-N-(4-(trifluoromethyl)phenyl)-[1,2,4]triazolo[1,5-a]pyrimidin-7-amine, 5-methyl-2-propoxy-N-(4-(trifluoromethyl)phenyl)-[1,2,4]triazolo[1,5-a]pyrimidin-7-amine, 2-ethynyl-5-methyl-N-(4-(trifluoromethyl)phenyl)-[1,2,4]triazolo[1,5-a]pyrimidin-7-amine, 5-methyl-7-(4-(trifluoromethyl)phenylamino)-[1,2,4]triazolo[1,5-a]pyrimidine-2-carboxamide, 2-(2-(dimethylamino)ethoxy)-5-methyl-N-(4-(trifluoromethyl)

phenyl)-[1,2,4]triazolo[1,5-a]pyrimidin-7-amine, 2,5-dimethyl-N-(4-(trifluoromethyl)phenyl)-[1,2,4]triazolo[1,5-a]pyrimidin-7-amine, 6-chloro-2,5-dimethyl-N-(4-(trifluoromethyl)phenyl)-[1,2,4]triazolo[1,5-a]pyrimidin-7-amine, or 2,5,6-trimethyl-N-(4-(trifluoromethyl)phenyl)-[1,2,4]triazolo[1,5-a]pyrimidin-7-amine, 2-(5-methyl-7-(4-(trifluoromethyl)phenylamino)-[1,2,4]triazolo[1,5-a]pyrimidin-2-yl)acetamide, 2-benzyl-5-methyl-N-(4-(trifluoromethyl)phenyl)-[1,2,4]triazolo[1,5-a]pyrimidin-7-amine, 5,6-dimethyl-N-(4-(trifluoromethyl)phenyl)-[1,2,4]triazolo[1,5-a]pyrimidin-7-amine, 2-(cyclopropylmethyl)-5-methyl-N-(4-(trifluoromethyl)phenyl)-[1,2,4]triazolo[1,5-a]pyrimidin-7-amine, or compounds listed in Table 4 and Table 5 below, or a pharmaceutically acceptable salt, solvate, stereoisomer, tautomer, or prodrug thereof.

Additional Therapeutic Agents

In one embodiment, the present methods for treating or preventing malaria further comprise the administration of a therapeutically effective amount of another therapeutic agent useful for inhibiting pyrimidine synthesis. In this embodiment, the time in which the therapeutic effect of the other therapeutic agent is exerted overlaps with the time in which the therapeutic effect of the compound of this invention is exerted.

The compositions of the invention can be combined or used in combination with other agents useful in the treatment, prevention, suppression or amelioration of malaria.

Such other agents, or drugs, may be administered, by a route and in an amount commonly used therefor, simultaneously or sequentially with a composition comprising a compound of the invention. In one embodiment, a pharmaceutical composition contains such other drugs in addition to the compound of the invention when a compound of the invention is used contemporaneously with one or more other drugs. Accordingly, the pharmaceutical compositions of the invention include those that also contain one or more other active ingredients or therapeutic agents, in addition to a compound of the invention.

In one embodiment, for the treatment or prevention of malaria, a compound of the invention can be administered with another therapeutic agent. The additional therapeutic agent may treat malaria directly, headache, malaise, anemia, splenomegaly, and/or fever. Examples of additional therapeutic agents include proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, and combinations thereof.

The present invention is not to be limited in scope by the specific embodiments disclosed in the examples which are intended as illustrations of a few embodiments of the invention and any embodiments that are functionally equivalent are within the scope of this invention. Indeed, various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence.

NON-LIMITING EXAMPLES

Example 1

Synthesis and Characterization of Compounds According to Formulae I-VIII

Compounds according to Formulae I-II of the invention and biological activities are presented in Tables 1 below.

TABLE 1

Compounds structure and activity.

| Note | Structure | $IC_{50}$ PfDHODH (μM) | $IC_{50}$ hDHODH (μM) | $EC_{50}$ P. falciparum (μM) |
|---|---|---|---|---|
| | 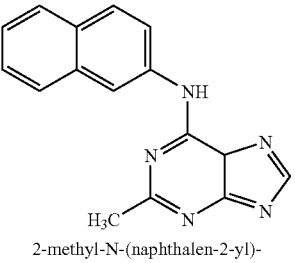 2-methyl-N-(naphthalen-2-yl)-9H-purin-6-amine | 0.44 ± 0.2 | >200 | 1.6 |
| | 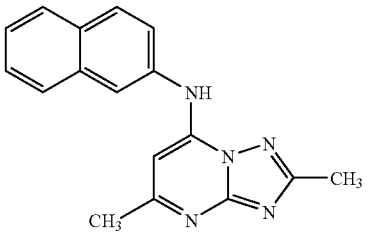 [SMILES: Cc1cc(Nc2ccc3ccccc3c2)n2nc(C)nc2n1] 2,5-Dimethyl-[1,2,4]triazolo[1,5-α]pyrimidin-7-yl)-naphthalen-2-yl-amine | 0.12 ± 0.02 | >200 | <0.15 |

| Note | Structure | IC$_{50}$ PfDHODH (μM) | IC$_{50}$ hDHODH (μM) | EC$_{50}$ P. falciparum (μM) |
|---|---|---|---|---|
| | 2,5-Dimethyl-[1,2,4]triazolo[1,5-α]pyrimidin-7-yl)-anthracen-2-yl-amine | 0.10 ± 0.0 | >200 | 0.23 ± 0.0014 |
Synthesis of 2-methyl-N-(naphthalen-2-yl)-9H-purin-6-amine
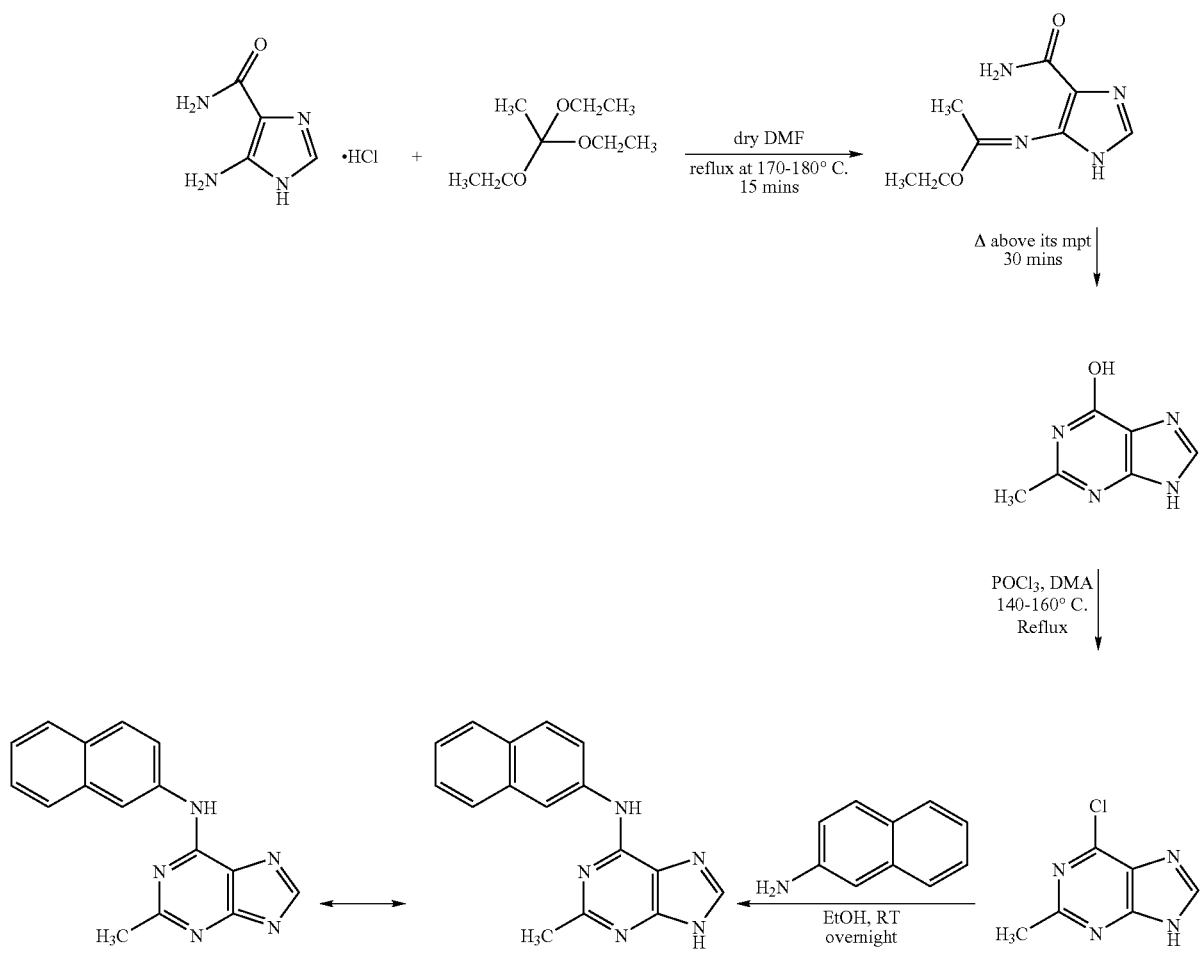
This compound is synthesized according the scheme above and is characterized as follows: melting point: 85° C. $^1$H NMR (300 MHz, DMSO-d6): δ 10.45 (brs, NH, exchangeable), 8.65 (s, 1H), 8.57 (s, 1H), 7.91-7.99 (m, 4H), 7.46-7.56 (m, 2H), 2.71 (s, 3H); MS m/z: 276.1 (M+H+).

Synthesis of 2,5-Dimethyl-[1,2,4]triazolo[1,5-a]pyrimidin-7-yl)-naphthalen-2-yl-amine

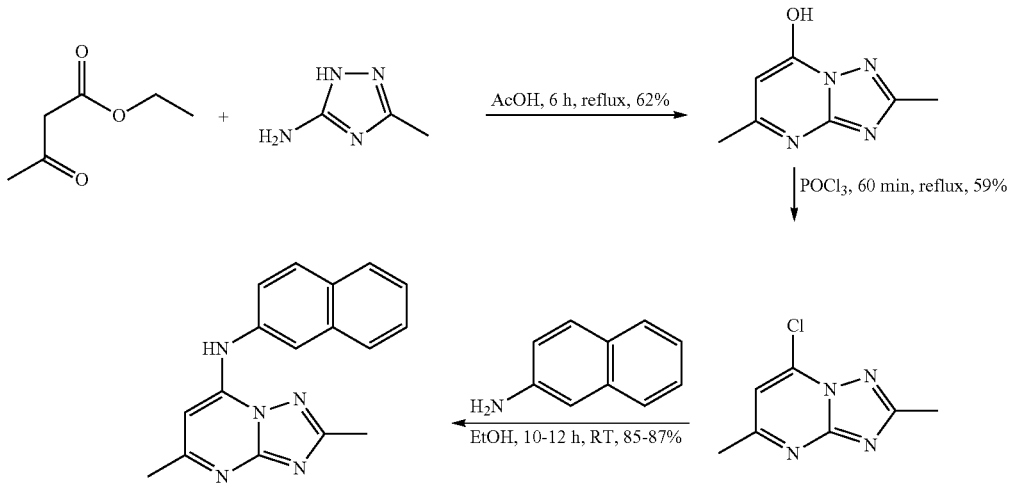

This compound is synthesized according the scheme above and is characterized as follows: melting point: 84° C. $^1$H NMR (300 MHz, DMSO-d6): δ 10.32 (brs, NH, exchangeable), 8.05-7.90 (m, 4H), 7.52-7.60 (m, 3H), 6.48 (s, 1H), 2.50 (s, 3H), 2.36 (s, 3H). MS m/z 290.1 (M+H+).

Synthesis of, 2,5-Dimethyl-[1,2,4]triazolo[1,5-α]pyrimidin-7-yl)-anthracen-2-yl-amine

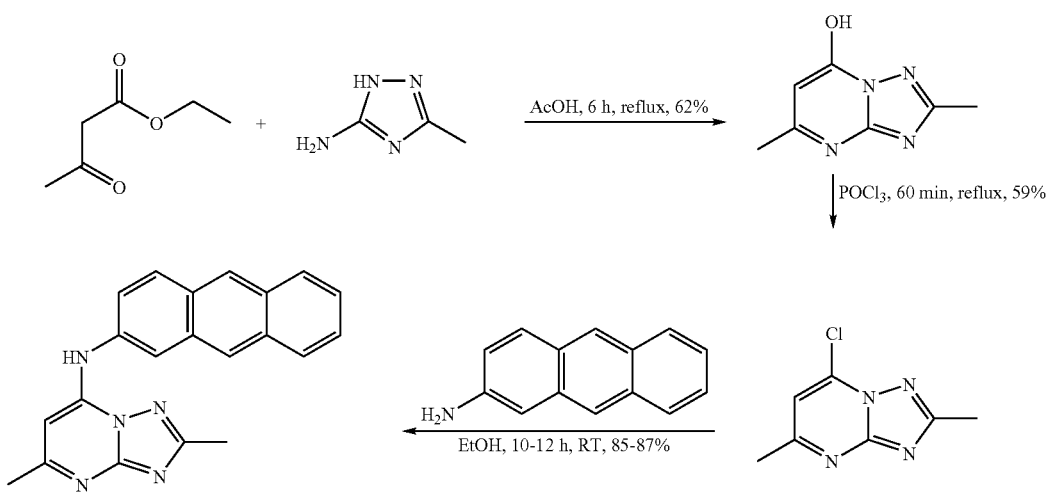

This compound is synthesized according the scheme above and is characterized as follows: melting point: 249° C. $^1$H NMR (300 MHz, DMSO-d6): δ 10.39 (brs, NH, exchangeable), 8.58 (d, J=9.0 Hz, 2H), 8.18 (d, J=9.0 Hz, 1H), 8.09-8.06 (m, 3H), 7.62 (d, J=9.0 Hz, 1H), 7.54-7.51 (m, 2H), 6.58 (s, 1H), 2.51 (s, 3H), 2.42 (s, 3H). MS m/z 340.3 (M+H+).

Compounds according to Formulae III-IV of the invention and biological activities are presented in Table 2 below.

TABLE 2

Compounds structure and activity.

| Structure | PfDHODH IC50 (μM) | PbDHODH IC50 (μM) | hDHODH IC50 (μM) | P. falciparum 3D7 EC50 (μM) |
|---|---|---|---|---|
| 5-Methyl-[1,2,4]triazolo[1,5-a]pyrimidin-7-yl)-(4-trifluoromethyl-phenyl)-amine | 0.3 ± 0.03; 0.3 ± 0.03; Ave = 0.3 ± 0 | 0.44 ± 0.027 | >100 | 0.35 ± 0.003 |
| 5-Methyl-[1,2,4]triazolo[1,5-a]pyrimidin-7-yl)-(3-chloro-phenyl)-amine | 1.45 ± 0.2; 1.4 ± 0.2; Ave = 1.42 ± 0.035 | | | 8.5 ± .002 |

Synthesis of 5-Methyl-[1,2,4]triazolo[1,5-a]pyrimidin-7-yl)-(4-trifluoromethyl-phenyl)-amine and 5-Methyl-[1,2,4]triazolo[1,5-a]pyrimidin-7-yl)-(3-chloro-phenyl)-amine

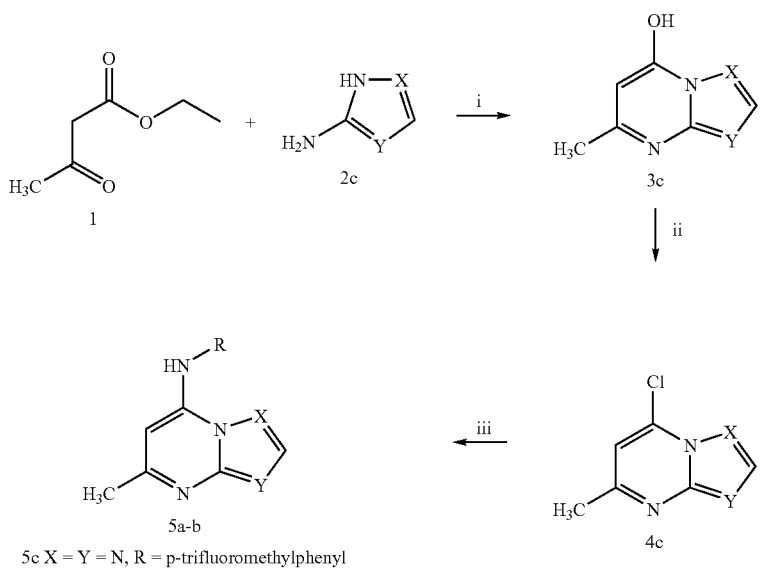

5c X = Y = N, R = p-trifluoromethylphenyl
5d X = Y = N, R = m-chlorophenyl

Reagents and conditions: (i) AcOH, 3.5-20 h, reflux, 58-80%; (ii) POCl$_3$, 30-90 min., reflux, 42-70%; (iii) RNH$_2$, EtOH, 3-15 h, rt, 76-82%.

Compounds 3c.

A mixture of 3-amino pyrazole/1H-Imidazol-2-ylamine/3-amino-1,2,4-triazole (2c) (20 mmol) and ethyl acetoacetate (20 mmol) was heated under reflux in acetic acid (10 ml) for 3.5-20 hours. The product was then cooled to room temperature, filtered, washed with ethanol/water, and dried under vacuum to give a white solid with 58-80% yield.

5-Methyl-[1,2,4]triazolo[1,5-a]pyrimidin-7-ol (3c)

mp. 287° C. $^1$H NMR (300 MHz, DMSO-$d_6$): δ 8.15 (s, 1H), 5.82 (s, 1H), 2.30 (s, 3H). MS m/z 151.1 (M+H$^+$).

Compounds 4c.

5-Methyl-pyrazolo[1,5-a]pyrimidin-7-ol/7-Methyl-imidazo[1,2-a]pyrimidin-5-ol/5-Methyl-[1,2,4]triazolo[1,5-a]pyrimidin-7-ol (3c) (6.5 mmol) was added to 1.82 ml (19.5 mmol) of phosphorus oxychloride and heated under reflux for 30-60 minutes. in a round bottom flask, during which time the solid dissolved and hydrogen chloride was evolved. Excess phosphorus oxychloride was removed by distillation at reduced pressure on a steam-bath and the residue triturated with ice water. Product was extracted from the aqueous mixture with methylene chloride, evaporated and purified by column chromatography using 60% EtOAc/Hexane at a yield of 42-70%.

7-Chloro-5-methyl-[1,2,4]triazolo[1,5-a]pyrimidine (4c)

mp. 150° C. $^1$H NMR (300 MHz, CDCl$_3$): δ 8.50 (s, 1H), 7.15 (s, 1H), 2.75 (s, 3H). MS m/z 169.1 (M+H$^+$).

Compounds 5c-d.

The appropriate aryl amine (1 mmol) was added to corresponding chloro compound 4c (1 mmol) in absolute ethanol (10 ml) and stirred at room temperature for 3-15 hours. Products were purified by column chromatography with CH$_2$Cl$_2$/MeOH/NH$_4$OH (23:1:1). Yields ranged from 76-82%.

5-Methyl-[1,2,4]triazolo[1,5-a]pyrimidin-7-yl)-(4-trifluoromethyl-phenyl)-amine (5c)

mp. 245° C. $^1$H NMR (300 MHz, DMSO-$d_6$): δ 10.51 (brs, NH, exchange-able), 8.56 (s, 1H), 7.81 (m, 2H), 7.71 (m, 2H), 6.69 (s, 1H), 2.46 (s, 3H). MS m/z 294.1 (M+H$^+$).

5-Methyl-[1,2,4]triazolo[1,5-a]pyrimidin-7-yl)-(3-chloro-phenyl)-amine (5d)

mp. 227° C. $^1$H NMR (300 MHz, DMSO-$d_6$): δ 10.31 (brs, NH, exchangeable), 8.52 (s, 1H), 7.54 (s, 1H), 7.50-7.48 (m, 2H), 7.36 (m, 1H), 6.49 (s, 1H), 2.44 (s, 3H). MS m/z 260.1 (M+H$^+$).

Compounds of the invention and biological activities are presented in Table 3 below.

TABLE 3

Compounds structure and activity.

| Structure | PfDHODH IC50 (µM) | PbDHODH IC50 (µM) | P. falciparum 3D7 EC50 (µM) |
|---|---|---|---|
| 5-Methyl-pyrazolo[1,5-a]pyrimidin-7-yl)-naphthalen-2-yl-amine | 0.4 ± 0.09; 0.4 ± 0.08; Ave = 0.4 ± 0 | 3.0 ± 0.3; 3.6 ± 0.3; Ave = 3.3 ± 0.4 | 0.99 ± 0.006; 1.1 ± 0.0084; Ave = 1.0 ± 0.07 |
| 7-Methyl-imidazo[1,2-a]pyrimidin-5-yl)-naphthalen-2-yl-amine | 0.16 ± 0.01; 0.14 ± 0.01; Ave = 0.15 ± 0.01 | 3.0 ± 0.3; 2.6 ± 0.2; Ave = 2.8 ± 0.3 | 0.20 ± 0.001 |

Synthesis of 5-Methyl-pyrazolo[1,5-a]pyrimidin-7-yl)-naphthalen-2-yl-amine and 7-Methyl-imidazo[1,2-a]pyrimidin-5-yl)-naphthalen-2-yl-amine

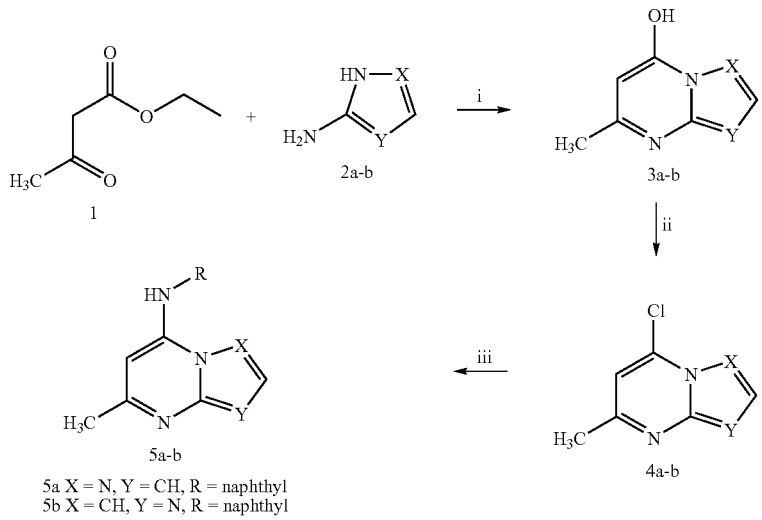

5a X = N, Y = CH, R = naphthyl
5b X = CH, Y = N, R = naphthyl

Reagents and conditions: (i) AcOH, 3.5-20 h, reflux, 58-80%; (ii) POCl₃, 30-90 min., reflux, 42-70%; (iii) RNH₂, EtOH, 3-15 h, rt, 76-82%.

Compounds 3a-b.

A mixture of 3-amino pyrazole/1H-Imidazol-2-ylamine/3-amino-1,2,4-triazole 2a-b (20 mmol) and ethyl acetoacetate (20 mmol) was heated under reflux in acetic acid (10 ml) for 3.5-20 hours. The product was then cooled to room temperature, filtered, washed with ethanol/water, and dried under vacuum to give a white solid with 58-80% yield.

5-Methyl-pyrazolo[1,5-a]pyrimidin-7-ol (3a)

mp. 298° C. $^1$H NMR (300 MHz, DMSO-$d_6$): δ 7.82 (s, 1H), 6.08 (s, 1H), 5.56 (s, 1H), 2.28 (s, 3H).

7-Methyl-imidazol-[1,2-a]pyrimidin-5-ol (3b)

mp. 229° C. $^1$H NMR (300 MHz, DMSO-$d_6$): δ 7.58 (s, 1H), 7.36 (s, 1H), 5.76 (s, 1H), 2.26 (s, 3H). MS m/z 150.1 (M+H$^+$).

Compounds 4a-b.

5-Methyl-pyrazolo[1,5-a]pyrimidin-7-ol/7-Methyl-imidazo[1,2-a]pyrimidin-5-ol/5-Methyl-[1,2,4]triazolo[1,5-a]pyrimidin-7-ol (3a-b) (6.5 mmol) was added to 1.82 ml (19.5 mmol) of phosphorus oxychloride (for compound 4b, dimethyl aniline also used along with phosphorus oxychloride) and heated under reflux for 30-60 minutes. in a round bottom flask, during which time the solid dissolved and hydrogen chloride was evolved. Excess phosphorus oxychloride was removed by distillation at reduced pressure on a steam-bath and the residue triturated with ice water. Product was extracted from the aqueous mixture with methylene chloride, evaporated and purified by column chromatography using 60% EtOAc/Hexane at a yield of 42-70%.

7-Chloro-5-methyl-pyrazolo[1,5-a]pyrimidine (4a)

mp. 39° C. $^1$H NMR (300 MHz, CDCl₃): δ 8.18 (s, 1H), 6.87 s, 1H), 6.68 (s, 1H), 2.62 (s, 3H).

5-Chloro-7-methyl-imidazo[1,2-a]pyrimidine (4b)

mp. 70° C. (dec). MS m/z 168.5 (M+H$^+$).

Compounds 5a-b.

The appropriate aryl amine (1 mmol) was added to corresponding chloro compound 4a-b (1 mmol) in absolute ethanol (10 ml) and stirred at room temperature for 3-15 hours. Products were purified by column chromatography with CH₂Cl₂/MeOH/NH₄OH (23:1:1). Yields ranged from 76-82%.

5-Methyl-pyrazolo[1,5-a]pyrimidin-7-yl)-naphthalen-2-yl-amine (5a)

mp. 138° C. $^1$H NMR (300 MHz, CDCl₃): δ 8.25 (brs, NH, exchangeable), 8.09 (s, 1H), 7.80-8.05 (m, 4H), 7.40-7.65 (m, 3H), 6.50 (s, 1H), 6.35 (s, 1H), 2.48 (s, 3H). MS m/z 275.1 (M+H$^+$).

7-Methyl-imidazo[1,2-a]pyrimidin-5-yl)-naphthalen-2-yl-amine (5b)

mp. 256° C. (dec). $^1$H NMR (300 MHz, CDCl₃): δ 7.50 (s, 1H), 7.37-7.39 (m, 5H), 6.80-6.94 (m, 3H), 5.69 (s, 1H), 2.25 (s, 3H). MS m/z 276.1 (M+H$^+$).

In other embodiments, examples of compounds according to the invention include but are not limited to those shown in Table 4, along with associated assay values determined according to the procedures described below:

TABLE 4

Compounds structure and activity.

| Structure | PfDHODH | PbDHODH | hDHODH |
|---|---|---|---|
| 7-(4-trifluoromethoxyphenylamino)-5-methyl-[1,2,4]triazolo[1,5-a]pyrimidine | +++ | + | + |
| 7-(biphenyl-4-ylamino)-5-methyl-[1,2,4]triazolo[1,5-a]pyrimidine | ++ | n.a. | n.a. |
| 7-(3-fluorophenylamino)-5-methyl-[1,2,4]triazolo[1,5-a]pyrimidine | ++ | + | + |
| 7-(4-fluorophenylamino)-5-methyl-[1,2,4]triazolo[1,5-a]pyrimidine | + | + | n.a. |
| 7-(2-fluorophenylamino)-5-methyl-[1,2,4]triazolo[1,5-a]pyrimidine | + | + | n.a. |

TABLE 4-continued
Compounds structure and activity.
| Structure | PfDHODH | PbDHODH | hDHODH |
|---|---|---|---|
| 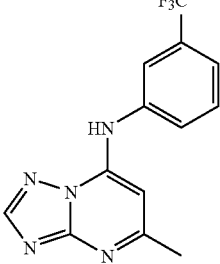 | + | + | + |
| 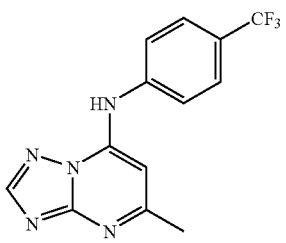 [SMILES: Cc1cc(Nc2ccc(C(F)(F)F)cc2)n2ncnc2n1] | +++ | +++ | + |
| 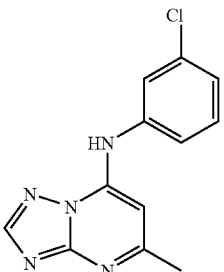 | +++ | + | + |
| 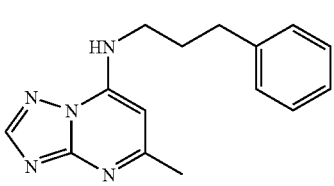 [SMILES: Cc1cc(NCCCc2ccccc2)n2ncnc2n1] | + | + | + |
| 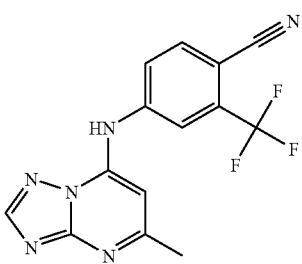 [SMILES: Cc1cc(Nc2ccc(C#N)c(C(F)(F)F)c2)n2ncnc2n1] | ++ | + | ++ |
| 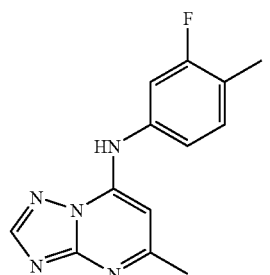 | +++ | ++ | + |

TABLE 4-continued

Compounds structure and activity.

| Structure | PfDHODH | PbDHODH | hDHODH |
|---|---|---|---|
| *[3-methyl-4-fluorophenyl-amino triazolopyrimidine]* | ++ | + | ++ |
| *[4-benzylphenyl-amino triazolopyrimidine]* | +++ | + | ++ |
| *[2-fluoro-4-methylphenyl-amino triazolopyrimidine]* | + | + | + |
| *[2-trifluoromethyl-benzimidazol-5-yl-amino triazolopyrimidine]* | + | + | + |
| *[4-trifluoromethoxyphenyl-amino triazolopyrimidine]* | +++ | + | + |

TABLE 4-continued
Compounds structure and activity.
| Structure | PfDHODH | PbDHODH | hDHODH |
|---|---|---|---|
| 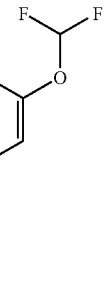 | +++ | + | n.a. |
| 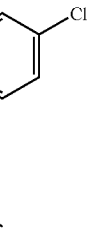 | +++ | ++ | + |
| 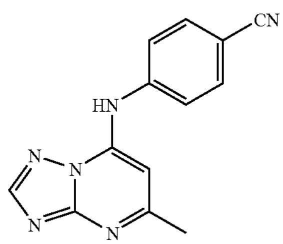 [SMILES: Cc1cc(Nc2ccc(C#N)cc2)n2ncnc2n1] | ++ | n.a. | n.a. |
|  | + | + | n.a. |
| 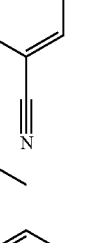 | + | + | n.a. |
|  | + | + | n.a. |

TABLE 4-continued

Compounds structure and activity.

| Structure | PfDHODH | PbDHODH | hDHODH |
|---|---|---|---|
| 3-methylphenyl-NH-[1,2,4]triazolo[1,5-a]pyrimidine-5-methyl | ++ | + | n.a. |
| 2-chlorophenyl-NH-[1,2,4]triazolo[1,5-a]pyrimidine-5-methyl | + | + | n.a. |
| 4-methylphenyl-NH-[1,2,4]triazolo[1,5-a]pyrimidine-5-methyl | ++ | + | n.a. |
| 4-methoxyphenyl-NH-[1,2,4]triazolo[1,5-a]pyrimidine-5-methyl | +++ | +++ | + |
| 4-nitrophenyl-NH-[1,2,4]triazolo[1,5-a]pyrimidine-5-methyl | ++ | ++ | n.a. |
| 4-bromophenyl-NH-[1,2,4]triazolo[1,5-a]pyrimidine-5-methyl | ++ | + | n.a. |

TABLE 4-continued

Compounds structure and activity.

| Structure | PfDHODH | PbDHODH | hDHODH |
|---|---|---|---|
| 4-ethylphenyl-NH-[1,2,4]triazolo[1,5-a]pyrimidin-7-yl, 5-methyl | +++ | ++ | + |
| 4-propylphenyl-NH-[1,2,4]triazolo[1,5-a]pyrimidin-7-yl, 5-methyl | +++ | ++ | + |
| 4-isopropylphenyl-NH-[1,2,4]triazolo[1,5-a]pyrimidin-7-yl, 5-methyl | +++ | +++ | + |
| 4-butylphenyl-NH-[1,2,4]triazolo[1,5-a]pyrimidin-7-yl, 5-methyl | +++ | ++ | + |
| 2,5-difluorophenyl-NH-[1,2,4]triazolo[1,5-a]pyrimidin-7-yl, 5-methyl | + | + | n.a. |
| 2,6-difluorophenyl-NH-[1,2,4]triazolo[1,5-a]pyrimidin-7-yl, 5-methyl | + | + | n.a. |

TABLE 4-continued

Compounds structure and activity.

| Structure | PfDHODH | PbDHODH | hDHODH |
|---|---|---|---|
| 2,3,4-trifluoroanilino-5-methyl-[1,2,4]triazolo[1,5-a]pyrimidine | + | + | + |
| 2,3-difluoroanilino-5-methyl-[1,2,4]triazolo[1,5-a]pyrimidine | + | + | n.a |
| 2,4,5-trifluoroanilino-5-methyl-[1,2,4]triazolo[1,5-a]pyrimidine | + | + | n.a |
| 2,4,6-trifluoroanilino-5-methyl-[1,2,4]triazolo[1,5-a]pyrimidine | + | + | + |
| 3,5-difluoroanilino-5-methyl-[1,2,4]triazolo[1,5-a]pyrimidine | ++ | + | + |

TABLE 4-continued

Compounds structure and activity.

| Structure | PfDHODH | PbDHODH | hDHODH |
|---|---|---|---|
| (3,4-difluorophenyl-NH-triazolopyrimidine-methyl) | ++ | ++ | n.a. |
| (benzothiazol-2-yl-NH-triazolopyrimidine-methyl) | n.a. | n.a. | n.a. |
| (benzothiazol-6-yl-NH-triazolopyrimidine-methyl) | n.a. | n.a. | n.a. |
| (4-vinylphenyl-NH-triazolopyrimidine-methyl) | +++ | ++ | n.a. |
| (4-pentylphenyl-NH-triazolopyrimidine-methyl) | +++ | + | n.a. |
| (4-hexylphenyl-NH-triazolopyrimidine-methyl) | ++ | + | n.a. |

TABLE 4-continued

Compounds structure and activity.

| Structure | PfDHODH | PbDHODH | hDHODH |
|---|---|---|---|
| [4-heptylphenyl-NH-triazolopyrimidine-methyl] | + | + | n.a. |
| [4-octylphenyl-NH-triazolopyrimidine-methyl] | + | + | n.a. |
| [3-CF3-4-methylphenyl-NH-triazolopyrimidine-methyl] | +++ | ++ | + |
| [3,4-dimethylphenyl-NH-triazolopyrimidine-methyl] | +++ | ++ | + |
| [3-CF3-4-Cl-phenyl-NH-triazolopyrimidine-methyl] | +++ | +++ | n.a. |

TABLE 4-continued

Compounds structure and activity.

| Structure | PfDHODH | PbDHODH | hDHODH |
|---|---|---|---|
| [3-fluoro-4-(trifluoromethyl)phenyl]amino triazolopyrimidine | +++ | +++ | + |
| [3,5-bis(trifluoromethyl)phenyl]amino triazolopyrimidine | + | + | + |
| (benzo[d][1,3]dioxol-5-yl)amino triazolopyrimidine | +++ | + | + |
| [4-bromo-3-(trifluoromethyl)phenyl]amino triazolopyrimidine | +++ | +++ | + |
| (4-tert-butylphenyl)amino triazolopyrimidine | +++ | +++ | n.a. |

TABLE 4-continued

Compounds structure and activity.

| Structure | PfDHODH | PbDHODH | hDHODH |
|---|---|---|---|
| (structure 1) | +++ | + | n.a. |
| (structure 2) | + | + | n.a. |
| (structure 3) | + | + | n.a. |
| (structure 4) | n.a. | n.a. | n.a. |

+++ IC$_{50}$ values <2 μM;
++ IC$_{50}$ values between 2-10 μM;
+ IC$_{50}$ values >10 μM; and
n.a. = not assigned.

Synthesis of 5-Methyl-[1,2,4]-triazolo[1,5-a]pyrimidin-7-yl)-(3-chloro-phenyl)-amine

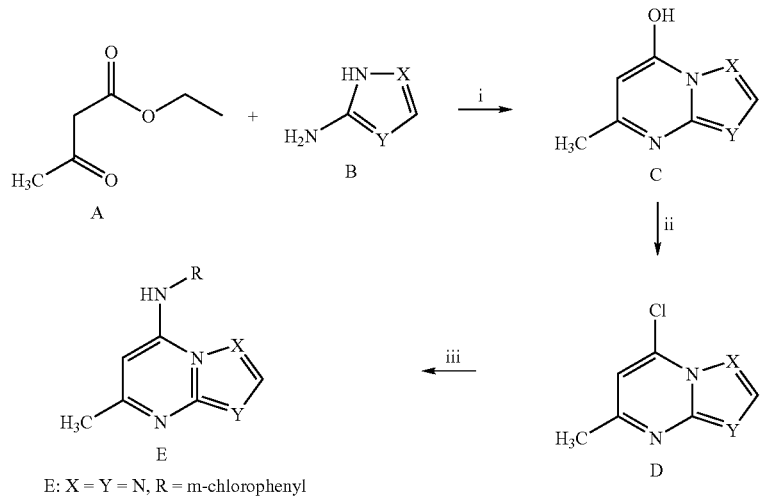

E: X = Y = N, R = m-chlorophenyl

Reagents and conditions: (i) AcOH, 3.5-20 h, reflux, 58-80%; (ii) POCl$_3$, 30-90 min., reflux, 42-70%; (iii) RNH$_2$, EtOH, 3-15 h, rt, 76-82%.

Compounds C.

A mixture of 3-amino pyrazole/1H-Imidazol-2-ylamine/3-amino-1,2,4-triazole (B) (20 mmol) and ethyl acetoacetate (A; 20 mmol) was heated under reflux in acetic acid (10 ml) for 3.5-20 hours. The product was then cooled to room temperature, filtered, washed with ethanol/water, and dried under vacuum to give a white solid with 58-80% yield.

5-Methyl-[1,2,4]triazolo[1,5-a]pyrimidin-7-ol (C)

mp. 287° C. $^1$H NMR (300 MHz, DMSO-d$_6$): δ 8.15 (s, 1H), 5.82 (s, 1H), 2.30 (s, 3H). MS m/z 151.1 (M+H).

Compounds D.

5-Methyl-pyrazolo[1,5-a]pyrimidin-7-ol/7-Methyl-imidazo[1,2-a]pyrimidin-5-ol/5-Methyl-[1,2,4]triazolo[1,5-a]-pyrimidin-7-ol (C) (6.5 mmol) was added to 1.82 ml (19.5 mmol) of phosphorus oxychloride and heated under reflux for 30-60 minutes. in a round bottom flask, during which time the solid dissolved and hydrogen chloride was evolved. Excess phosphorus oxychloride was removed by distillation at reduced pressure on a steam-bath and the residue triturated with ice water. Product was extracted from the aqueous mixture with methylene chloride, evaporated and purified by column chromatography using 60% EtOAc/Hexane at a yield of 42-70%.

7-Chloro-5-methyl-[1,2,4]triazolo[1,5-a]pyrimidine (D)

mp. 150° C. $^1$H NMR (300 MHz, CDCl$_3$): δ 8.50 (s, 1H), 7.15 (s, 1H), 2.75 (s, 3H). MS m/z 169.1 (M+H$^+$).

Compound E.

The appropriate aryl amine (1 mmol) was added to corresponding chloro compound D (1 mmol) in absolute ethanol (10 ml) and stirred at room temperature for 3-15 hours. Products were purified by column chromatography using CH$_2$Cl$_2$/MeOH/NH$_4$OH (23:1:1). Yield ranged from 76-82%.

The following compounds were prepared in a manner similar to that as described above; their physicochemical properties are listed below:

(2-Fluoro-phenyl)-(5-methyl-[1,2,4]triazolo[1,5-a]pyrimidin-7-yl)-amine

Mp 180° C. $^1$H NMR (300 MHz, CDCl$_3$): δ 8.49 (s, 1H), 7.58 (m, 1H), 7.41 (m, 1H), 7.35-7.30 (m, 2H), 6.33 (s, 1H), 2.64 (s, 3H). MS m/z 244 [M+H]$^+$.

(2-Chloro-phenyl)-(5-methyl-[1,2,4]triazolo[1,5-a]pyrimidin-7-yl)-amine

Mp 174° C. (lit.$^{35}$ 174° C.). $^1$H NMR (300 MHz, DMSO-d$_6$): δ 10.14 (brs, NH, exchangeable), 8.49 (s, 1H), 7.68 (m, 1H), 7.62-7.39 (m, 3H), 5.82 (s, 1H), 2.36 (s, 3H). MS m/z 260.2 [M+H]$^+$.

(5-Methyl-[1,2,4]triazolo[1,5-a]pyrimidin-7-yl)-o-tolyl-amine

Mp 183° C. (lit.$^{35}$ 179-180° C.). $^1$H NMR (300 MHz, DMSO-d$_6$): δ 9.92 (brs, NH, exchangeable), 8.48 (s, 1H), 7.47-7.26 (m, 4H), 5.73 (s, 1H), 2.33 (s, 3H), 2.21 (s, 3H). MS m/z 240.1 [M+H]$^+$.

(5-Methyl-[1,2,4]triazolo[1,5-a]pyrimidin-7-yl)-(2-trifluoromethyl-phenyl)-amine Mp 223° C. $^1$H NMR (300 MHz, DMSO-d$_6$): δ 10.15 (brs, NH, exchangeable), 8.52 (s, 1H), 8.05-7.56 (m, 4H), 5.85 (s, 1H), 2.39 (s, 3H). MS m/z 294.1 [M+H]$^+$.

2-(5-Methyl-[1,2,4]triazolo[1,5-a]pyrimidin-7-ylamino)-benzonitrile

Mp 246° C. $^1$H NMR (300 MHz, DMSO-d$_6$): δ 10.54 (brs, NH, exchangeable), 8.51 (s, 1H), 7.98 (m, 1H), 7.82 (m, 1H), 7.55 (m, 2H), 6.08 (s, 1H), 2.38 (s, 3H). MS m/z 251 [M+H]$^+$.

(3-Fluoro-phenyl)-(5-methyl-[1,2,4]triazolo[1,5-a]pyrimidin-7-yl)-amine

Mp 223° C. $^1$H NMR (300 MHz, DMSO-d$_6$): δ 10.35 (brs, NH, exchangeable), 8.54 (s, 1H), 7.51 (m, 1H), 7.35 (m, 2H), 7.11 (m, 1H), 6.58 (s, 1H), 2.47 (s, 3H). MS m/z 244 [M+H]$^+$.

(3-Chloro-phenyl)-(5-methyl-[1,2,4]triazolo[1,5-a]pyrimidin-7-yl)-amine

Mp 227° C. (lit.[36] 228° C.). $^1$H NMR (300 MHz, DMSO-$d_6$): δ 10.31 (brs, NH, exchangeable), 8.52 (s, 1H), 7.54 (s, 1H), 7.50-7.48 (m, 2H), 7.36 (m, 1H), 6.49 (s, 1H), 2.44 (s, 3H). MS m/z 260.1 [M+H]$^+$.

(5-Methyl-[1,2,4]triazolo[1,5-a]pyrimidin-7-yl)-m-tolyl-amine

Mp 194° C. $^1$H NMR (300 MHz, DMSO-$d_6$): δ 10.10 (brs, NH, exchangeable), 8.48 (s, 1H), 7.35 (m, 1H), 7.25 (m, 2H), 7.12 (m, 1H), 6.34 (s, 1H), 2.40 (s, 3H), 2.33 (s, 3H). MS m/z 240 [M+H]$^+$.

(5-Methyl-[1,2,4]triazolo[1,5-a]pyrimidin-7-yl)-(3-trifluoromethyl-phenyl)-amine Mp 200° C. $^1$H NMR (300 MHz, DMSO-$d_6$): δ 10.43 (brs, NH, exchangeable), 8.55 (s, 1H), 7.82 (m, 2H), 7.72 (m, 1H), 7.65 (m, 1H), 6.53 (s, 1H), 2.46 (s, 3H). MS m/z 294.1 [M+H]$^+$.

(4-Fluoro-phenyl)-(5-methyl-[1,2,4]triazolo[1,5-a]pyrimidin-7-yl)-amine

Mp 224° C. $^1$H NMR (300 MHz, DMSO-$d_6$): δ 10.12 (brs, NH, exchangeable), 8.49 (s, 1H), 7.51-7.47 (m, 2H), 7.35-7.29 (m, 2H), 6.29 (s, 1H), 2.41 (s, 3H). MS m/z 244.1 [M+H]$^+$.

(4-Chloro-phenyl)-(5-methyl-[1,2,4]triazolo[1,5-a]pyrimidin-7-yl)-amine

Mp 267° C. $^1$H NMR (300 MHz, DMSO-$d_6$): δ 10.22 (brs, NH, exchangeable), 8.47 (s, 1H), 7.55-7.45 (m, 4H), 6.42 (s, 1H), 2.42 (s, 3H). MS m/z 260.1 [M+H]$^+$.

(4-Bromo-phenyl)-(5-methyl-[1,2,4]triazolo[1,5-a]pyrimidin-7-yl)-amine

Mp 268° C. (lit.[36] 265° C.). $^1$H NMR (300 MHz, DMSO-$d_6$): δ 10.24 (brs, NH, exchangeable), 8.50 (s, 1H), 7.65 (d, J=8.7 Hz, 2H), 7.45 (d, J=8.7 Hz, 2H), 6.46 (s, 1H), 2.43 (s, 3H). MS m/z 305.9 [M+H]$^+$.

(5-Methyl-[1,2,4]triazolo[1,5-a]pyrimidin-7-yl)-p-tolyl-amine

Mp 206° C. $^1$H NMR (300 MHz, DMSO-$d_6$): δ 10.09 (brs, NH, exchangeable), 8.48 (s, 1H), 7.35-7.27 (m, 4H), 6.29 (s, 1H), 2.40 (s, 3H), 2.35 (s, 3H). MS m/z 240 [M+H]$^+$.

(5-Methyl-[1,2,4]triazolo[1,5-a]pyrimidin-7-yl)-(4-trifluoromethyl-phenyl)-amine Mp 244° C. $^1$H NMR (300 MHz, DMSO-$d_6$): δ 10.51 (brs, NH, exchangeable), 8.52 (s, 1H), 7.81 (m, 2H), 7.71 (m, 2H), 6.69 (s, 1H), 2.46 (s, 3H). MS m/z 294.1 [M+H]$^+$.

(4-Methoxy-phenyl)-(5-methyl-[1,2,4]triazolo[1,5-a]pyrimidin-7-yl)-amine

Mp 212° C. (lit.[36] 211° C.). $^1$H NMR (300 MHz, DMSO-$d_6$): δ 10.01 (brs, NH, exchangeable), 8.46 (s, 1H), 7.35 (d, J=8.4 Hz, 2H), 7.05 (d, J=8.4 Hz, 2H), 6.16 (s, 1H), 3.80 (s, 3H), 2.38 (s, 3H). MS m/z 256.1 [M+H]$^+$.

(5-Methyl-[1,2,4]triazolo[1,5-a]pyrimidin-7-yl)-(4-trifluoromethoxy-phenyl)-amine Mp 214° C. $^1$H NMR (300 MHz, CDCl$_3$): δ 8.37 (s, 1H), 7.95 (s, 1H), 7.44-7.39 (m, 3H), 6.37 (s, 1H), 2.58 (s, 3H). MS m/z 310.1 [M+H]$^+$.

(4-Difluoromethoxy-phenyl)-(5-methyl-[1,2,4]triazolo[1,5-a]pyrimidin-7-yl)-amine (20)

Mp 200° C. $^1$H NMR (300 MHz, DMSO-$d_6$): δ 10.23 (brs, NH, exchangeable), 8.50 (s, 1H), 7.52-7.49 (m, 2H), 7.30-7.27 (m, 3H), 6.34 (s, 1H), 2.41 (s, 3H). MS m/z 292.1 [M+H]$^+$.

(5-Methyl-[1,2,4]triazolo[1,5-a]pyrimidin-7-yl)-(4-nitro-phenyl)-amine

Mp 338° C. $^1$H NMR (300 MHz, DMSO-$d_6$): δ 8.55 (s, 1H), 8.30 (d, J=9 Hz, 2H), 7.71 (m, 2H), 6.85 (s, 1H), 2.49 (s, 3H). MS m/z 271 [M+H]$^+$.

Biphenyl-4-yl-(5-methyl-[1,2,4]triazolo[1,5-a]pyrimidin-7-yl)-amine

Mp 114° C. $^1$H NMR (300 MHz, DMSO-$d_6$): δ 10.31 (brs, NH, exchangeable), 8.52 (s, 1H), 7.78-7.69 (m, 4H), 7.56-7.37 (m, 4H), 7.21 (m, 1H), 6.49 (s, 1H), 2.43 (s, 3H). MS m/z 302.1 [M+H]$^+$.

(4-Benzyl-phenyl)-(5-methyl-[1,2,4]triazolo[1,5-a]pyrimidin-7-yl)-amine

Mp 190° C. $^1$H NMR (300 MHz, DMSO-$d_6$): δ 10.11 (brs, NH, exchangeable), 8.48 (s, 1H), 7.35-7.21 (m, 9H), 6.34 (s, 1H), 3.97 (s, 2H), 2.40 (s, 3H). MS m/z 316.2 [M+H]$^+$.

(2,3-Difluoro-phenyl)-(5-methyl-[1,2,4]triazolo[1,5-a]pyrimidin-7-yl)-amine

Mp 231° C. $^1$H NMR (300 MHz, DMSO-$d_6$): δ 8.76 (s, 1H), 7.57-7.48 (m, 1H), 7.41-7.33 (m, 2H), 6.33 (s, 1H), 2.46 (s, 3H). MS m/z 262.1 [M+H]$^+$.

(2,5-Difluoro-phenyl)-(5-methyl-[1,2,4]-triazolo[1,5-a]pyrimidin-7-yl)-amine Mp 227° C. $^1$H NMR (300 MHz, DMSO-$d_6$): δ 10.21 (brs, NH, exchangeable), 8.53 (s, 1H), 7.54-7.44 (m, 2H), 7.35-7.28 (m, 1H), 6.12 (s, 1H), 2.43 (s, 3H). MS m/z 262.1 [M+H]$^+$.

(2,6-Difluoro-phenyl)-(5-methyl-[1,2,4]triazolo[1,5-a]pyrimidin-7-yl)-amine

Mp 231° C. $^1$H NMR (300 MHz, DMSO-$d_6$): δ 8.76 (s, 1H), 7.62-7.53 (m, 1H), 7.39-7.34 (m, 2H), 6.17 (s, 1H), 2.45 (s, 3H). MS m/z 262 [M+H]$^+$.

(5-Methyl-[1,2,4]triazolo[1,5-a]pyrimidin-7-yl)-(2,3,4-trifluoro-phenyl)-amine Mp 246° C. $^1$H NMR (300 MHz, DMSO-d$_6$): δ 8.73 (s, 1H), 7.55-7.37 (m, 2H), 6.34 (s, 1H), 2.45 (s, 3H). MS m/z 280.2 [M+H]$^+$.

(5-Methyl-[1,2,4]triazolo[1,5-a]pyrimidin-7-yl)-(2,4,5-trifluoro-phenyl)-amine Mp 272° C. $^1$H NMR (300 MHz, DMSO-d$_6$): δ 8.67 (s, 1H), 7.89-7.72 (m, 2H), 6.25 (s, 1H), 2.44 (s, 3H). MS m/z 280.1 [M+H]$^+$.

(5-Methyl-[1,2,4]triazolo[1,5-a]pyrimidin-7-yl)-(2,4,6-trifluoro-phenyl)-amine Mp 178° C. $^1$H NMR (300 MHz, DMSO-d$_6$): δ 10.02 (brs, NH, exchangeable), 8.54 (s, 1H), 7.51-7.46 (m, 2H), 6.08 (s, 1H), 2.41 (s, 3H). MS m/z 280.1 [M+H]$^+$.

(5-Methyl-[1,2,4]triazolo[1,5-a]pyrimidin-7-yl)-(2,3,5,6-tetrafluoro-phenyl)-amine Mp 211° C. $^1$H NMR (300 MHz, DMSO-d$_6$): δ 13.25 (brs, NH, exchangeable), 8.53 (s, 1H), 8.18 (s, 1H), 5.83 (s, 1H), 2.32 (s, 3H). MS m/z 298.1 [M+H]$^+$.

(5-Methyl-[1,2,4]triazolo[1,5-a]pyrimidin-7-yl)-(2,3,4,5,6-pentafluorophenyl)-amine Mp 278° C. $^1$H NMR (300 MHz, DMSO-d$_6$): δ 13.20 (brs, NH, exchangeable), 8.18 (s, 1H), 5.83 (s, 1H), 2.32 (s, 3H). MS m/z 316.2 [M+H]$^+$.

(2-Fluoro-4-methyl-phenyl)-(5-methyl-[1,2,4]triazolo[1,5-a]pyrimidin-7-yl)-amine Mp 208° C. $^1$H NMR (300 MHz, DMSO-d$_6$): δ 10.05 (brs, NH, exchangeable), 8.50 (s, 1H), 7.38-7.12 (m, 3H), 5.95 (s, 1H), 2.35 (s, 3H). MS m/z 258.1 [M+H]$^+$.

(3,4-Difluoro-phenyl)-(5-methyl-[1,2,4]triazolo[1,5-a]pyrimidin-7-yl)-amine

Mp 265° C. $^1$H NMR (300 MHz, DMSO-d$_6$): δ 8.54 (s, 1H), 7.62-7.51 (m, 2H), 7.38-7.31 (m, 1H), 6.47 (s, 1H), 2.44 (s, 3H). MS m/z 262.1 [M+H]$^+$.

(3,5-Difluoro-phenyl)-(5-methyl-[1,2,4]triazolo[1,5-a]pyrimidin-7-yl)-amine

Mp 256° C. $^1$H NMR (300 MHz, DMSO-d6): δ 10.41 (brs, NH, exchangeable), 8.54 (s, 1H), 7.25 (m, 2H), 7.15 (m, 1H), 6.73 (s, 1H), 2.49 (s, 3H). MS m/z 262.1 [M+H]$^+$.

(3,5-Bis-trifluoromethyl-phenyl)-(5-methyl-[1,2,4]triazolo[1,5-a]pyrimidin-7-yl)-amine Mp 257° C. $^1$H NMR (300 MHz, DMSO-d$_6$): δ 10.57 (brs, NH, exchangeable), 8.53 (s, 1H), 8.13 (m, 2H), 7.96 (m, 1H), 6.64 (s, 1H), 2.45 (s, 3H). MS m/z 362.2 [M+H]$^+$.

(4-Fluoro-3-methyl-phenyl)-(5-methyl-[1,2,4]triazolo[1,5-a]pyrimidin-7-yl)-amine (36)

Mp 231° C. $^1$H NMR (300 MHz, DMSO-d$_6$): δ 10.09 (brs, NH, exchangeable), 8.48 (s, 1H), 7.36-7.23 (m, 3H), 6.25 (s, 1H), 2.40 (s, 3H), 2.26 (s, 3H). MS m/z 258.1 [M+H]$^+$.

(4-Chloro-3-trifluoromethyl-phenyl)-(5-methyl-[1,2,4]triazolo[1,5-a]pyrimidin-7-yl)-amine Mp 233° C. $^1$H NMR (300 MHz, DMSO-d$_6$): δ 10.42 (brs, NH, exchangeable), 8.52 (s, 1H), 7.93 (s, 1H), 7.80 (m, 2H), 6.62 (s, 1H), 2.45 (s, 3H). MS m/z 328.2 [M+H]$^+$.

(4-Bromo-3-trifluoromethyl-phenyl)-(5-methyl-[1,2,4]triazolo[1,5-a]pyrimidin-7-yl)-amine Mp 243° C. $^1$H NMR (300 MHz, DMSO-d$_6$): δ 10.41 (brs, NH, exchangeable), 8.52 (s, 1H), 7.92 (s, 1H), 7.68 (m, 2H), 6.61 (s, 1H), 2.40 (s, 3H). MS m/z 373.9 [M+H]$^+$.

(5-Methyl-[1,2,4]triazolo[1,5-a]pyrimidin-7-yl)-(4-methyl-3-trifluoromethyl-phenyl)-amine Mp 200° C. $^1$H NMR (300 MHz, DMSO-d$_6$): δ 10.28 (brs, NH, exchangeable), 8.50 (s, 1H), 7.74 (s, 1H), 7.68 (d, J=8.1 Hz, 1H), 7.55 (d, J=8.4 Hz, 1H), 6.41 (s, 1H), 2.47 (s, 3H), 2.43 (s, 3H). MS m/z 308.2 [M+H]$^+$.

(3,4-Dimethyl-phenyl)-(5-methyl-[1,2,4]triazolo[1,5-a]pyrimidin-7-yl)-amine

Mp 224° C. $^1$H NMR (300 MHz, DMSO-d$_6$): δ 10.01 (brs, NH, exchangeable), 8.44 (s, 1H), 7.46-7.06 (m, 3H), 6.20 (s, 1H), 2.37 (s, 3H), 2.23 (s, 6H). MS m/z 254.2 [M+H]$^+$.

4-(5-Methyl-[1,2,4]triazolo[1,5-a]pyrimidin-7-ylamino)-2-trifluoromethyl-benzonitrile Mp 264° C. $^1$H NMR (300 MHz, DMSO-d$_6$): δ 8.55 (s, 1H), 8.20 (m, 1H), 8.05 (s, 1H), 7.95 (m, 1H), 6.90 (s, 1H), 2.48 (s, 3H). MS m/z 319.1 [M+H]$^+$.

(3-Fluoro-4-methyl-phenyl)-(5-methyl-[1,2,4]triazolo[1,5-a]pyrimidin-7-yl)-amine Mp 251° C. $^1$H NMR (300 MHz, DMSO-d$_6$): δ 10.20 (brs, NH, exchangeable), 8.48 (s, 1H), 7.36-7.23 (m, 3H), 6.43 (s, 1H), 2.41 (s, 3H), 2.25 (s, 3H). MS m/z 258.1 [M+H]$^+$.

(3-Fluoro-4-trifluoromethyl-phenyl)-(5-methyl-[1,2,4]triazolo[1,5-a]pyrimidin-7-yl)-amine Mp 247° C. $^1$H NMR (300 MHz, DMSO-d$_6$): δ 10.65 (brs, NH, exchangeable), 8.56 (s, 1H), 7.85-7.78 (m, 1H), 7.68-7.60 (m, 1H), 7.55-7.45 (m, 1H), 6.88 (s, 1H), 2.50 (s, 3H). MS m/z 312.2 [M+H]$^+$.

In some other embodiments, examples of compounds according to the invention include, but are not limited to, those shown in Table 5, along with associated assay values determined according to the procedures described below:

TABLE 5

Compounds structure and activity.

| Structure | PfDHODH IC$_{50}$ (μM) | EC$_{50}$ P. falciparum 3D7 cells (μM) |
|---|---|---|
| 2,5-dimethyl-N-(4-(trifluoromethyl)phenyl)-[1,2,4]triazolo[1,5-a]pyrimidin-7-amine | 0.65 ± 0.31 | 0.93 ± 0.018 |
| 6-chloro-2,5-dimethyl-N-(4-(trifluoromethyl)phenyl)-[1,2,4]triazolo[1,5-a]pyrimidin-7-amine | 0.62 ± 0.08 | 7.1 ± 0.04 |
| 2,5,6-trimethyl-N-(4-(trifluoromethyl)phenyl)-[1,2,4]triazolo[1,5-a]pyrimidin-7-amine | 3.0 ± 0.46 | 3.6 ± 0.004 |
| 5,6-dimethyl-N-(4-(trifluoromethyl)phenyl)-[1,2,4]triazolo[1,5-a]pyrimidin-7-amine | 1.2 ± 0.33 | 2.7 ± 0.009 |

TABLE 5-continued

Compounds structure and activity.

| Structure | PfDHODH IC$_{50}$ (μM) | EC$_{50}$ P. falciparum 3D7 cells (μM) |
|---|---|---|
| 6-chloro-5-methyl-N-(4-(trifluoromethyl)phenyl)-[1,2,4]triazolo[1,5-a]pyrimidin-7-amine | 0.34 ± 0.06 | 2.7 μM ± 0.03 μM |
| 5-methyl-N-(4-(trifluoromethyl)phenyl)-[1,2,4]triazolo[1,5-a]pyrimidin-7-amine | 0.077 ± 0.008 | 0.33 ± 0.02 |
| | 0.07061 | 0.08-0.12 |
| | 0.07061 | 0.08-0.12 |
| 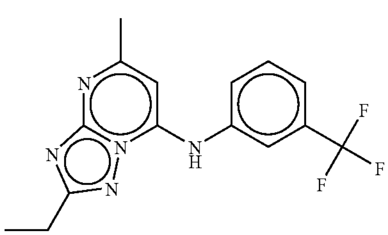 | 1.175 | |

TABLE 5-continued

Compounds structure and activity.

| Structure | PfDHODH IC$_{50}$ (μM) | EC$_{50}$ P. falciparum 3D7 cells (μM) |
|---|---|---|
| 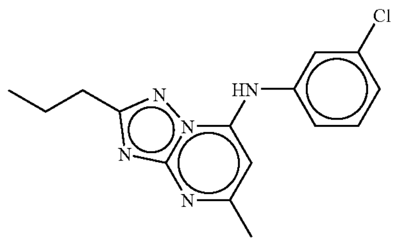 | 0.2469 | |
| 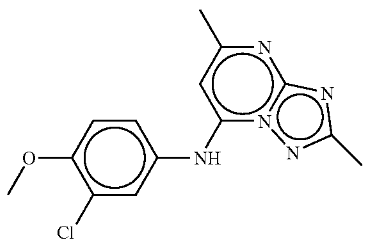 | 0.3749 | |
| 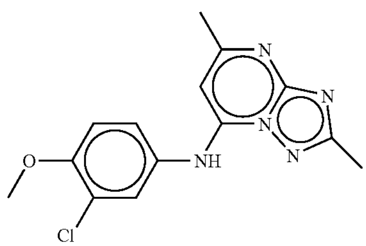 | 0.3257 | |
| 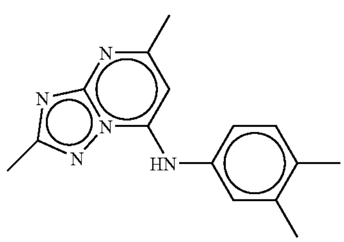 | 0.08141 | |
| 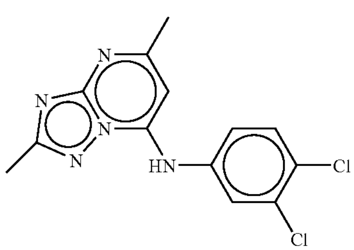 | 0.0752 | |
| 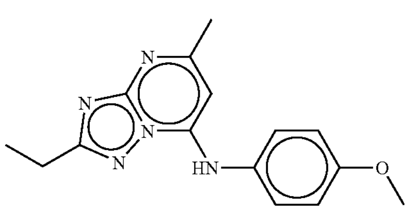 | 2.25 | |

TABLE 5-continued

Compounds structure and activity.

| Structure | PfDHODH IC$_{50}$ (μM) | EC$_{50}$ P. falciparum 3D7 cells (μM) |
|---|---|---|
| ethyl-triazolopyrimidine-NH-(4-iodophenyl) | 0.03789 | |
| methyl-triazolopyrimidine-NH-(3-trifluoromethylphenyl) | 0.2853 | |
| methyl-triazolopyrimidine-NH-(4-chloro-3-methylphenyl) | 1.386 | |
| propyl-triazolopyrimidine-NH-(3-chloro-4-methylphenyl) | 0.132 | |
| (3-ethylphenyl)-NH-triazolopyrimidine | 0.641 | |
| triazolopyrimidine-NH-(3-chloro-4-methylphenyl) | 0.2401 | |
| (3-chloro-4-methoxyphenyl)-NH-triazolopyrimidine | 0.315 | |

TABLE 5-continued
Compounds structure and activity.
| Structure | PfDHODH IC$_{50}$ (μM) | EC$_{50}$ P. falciparum 3D7 cells (μM) |
|---|---|---|
| 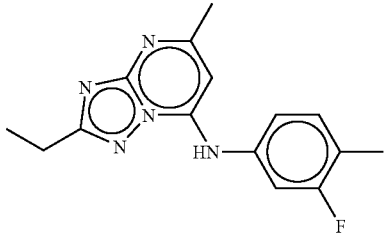 | 0.06634 | |
| 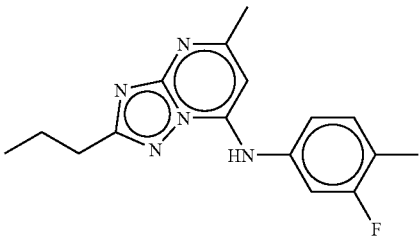 | 0.2769 | |
| 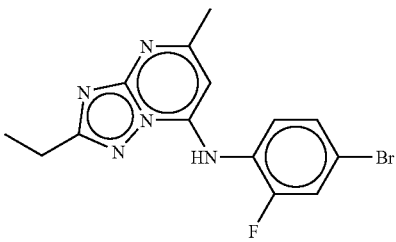 | 0.3955 | |
| 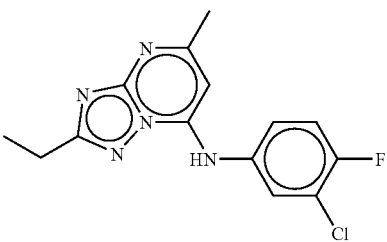 | 0.1454 | |
| 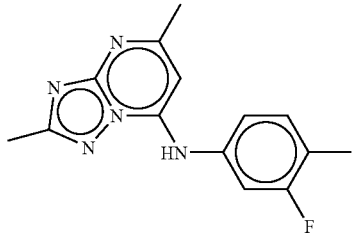 | 0.629 | |
| 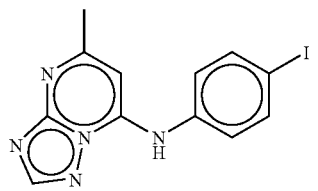 | 0.1513 | |

TABLE 5-continued

Compounds structure and activity.

| Structure | PfDHODH IC$_{50}$ (μM) | EC$_{50}$ P. falciparum 3D7 cells (μM) |
|---|---|---|
| (structure) | 0.566 | |
| 6-chloro-5-methyl-N-(4-(trifluoromethyl)phenyl)-[1,2,4]triazolo[1,5-a]pyrimidin-7-amine | 0.34 ± 0.06 | 2.7 ± 0.03 |
| 7-methyl-N-(4-(trifluoromethyl)phenyl)imidazo[1,2-a]pyrimidin-5-amine | 0.077 ± 0.008 | 0.33 ± 0.02 |
| (structure) | 6.3 ± 0.95 | |
| (structure) | 0.99 ± 0.18 | |

TABLE 5-continued

Compounds structure and activity.

| Structure | PfDHODH IC$_{50}$ (μM) | EC$_{50}$ P. falciparum 3D7 cells (μM) |
|---|---|---|
| morpholine-phenyl-HN-[1,2,4]triazolo[1,5-a]pyrimidine-CH$_3$ | >100 | |
| tetrahydronaphthyl-HN-[1,2,4]triazolo[1,5-a]pyrimidine-CH$_3$ | 0.05 ± 0.008 | |
| indanyl-HN-[1,2,4]triazolo[1,5-a]pyrimidine-CH$_3$ | 0.116 ± 0.03 | |
| 4-SF$_5$-phenyl-HN-[1,2,4]triazolo[1,5-a]pyrimidine-CH$_3$ | 0.117 ± 0.01 | |

Example 2

Biological Evaluation of the Compounds of Formulae I-VIII

In addition to the extensive literature disclosing the role of DHOHD in malaria, described here are assays useful for testing the compounds of the present invention.

Assays

I. Measurement of Enzyme Inhibition.

For studying inhibition of *Plasmodium* or human DHODH enzyme, two assays that are in routine use are described, for example, in Baldwin, et al. (2002) *J Biol Chem.*, 277, 41827-41834, and Baldwin, et al. (2005) *J Biol. Chem.*, 280. 21847-21853.

Briefly, these assays are as follows:

A calorimetric assay that monitors 2,6-dichloroindophenol (DCIP) reduction at 600 nm (e=18.8 mM$^{-1}$cm$^{-1}$) is used for inhibition studies. Briefly, the assay solution contained 100 mM HEPES, pH 8.0, 150 mM NaCl, 10% glycerol, 0.1% Triton X-100, 20 micro molar COQ$_D$ (coenzyme Q$_D$), 200 micro molar L-dihydroorotate, and 120 micro molar DCIP. Reactions are initiated by addition of enzyme to a final concentration in the range of about 5 nm to about 50 nM while maintaining the temperature of a circulating water bath at 25° C.

Alternatively, for potent compounds activity was determined by directly measuring the production of orotic acid at 296 nm (ϵ=4.3 mM$^{-1}$cm$^{-1}$). Assay solutions were prepared as discussed above, except that DCIP is not present and the solution is depleted of oxygen by the inclusion of an oxidase/reductase system, such as, 0.1 mg/ml of glucose oxidase, 0.02 mg/ml catalase and 50 mM glucose. The data obtained is fitted to equation 1, to determine the IC$_{50}$ values of the representative compounds.

$$v_i = \frac{v_o}{1 + \frac{[I]}{IC_{50}}}$$ Equation 1

II. In Vitro Evaluation of Compound Efficacy on the Human Malaria Parasite, P. falciparum.

To study inhibition of cell proliferation, $^3$H-hypoxanthine uptake is measured in drug-treated, P. falciparum-infected erythrocytes grown in culture, pursuant to the methodology of Desjardins, et al. (1979) Antimicrobial Agents and Chemotherapy 16, 710-718, and Zhang and Rathod (2002) Science 296, 545-547.

III. Pharmacokinetic Analysis.

Pharmacokinetics of the inventive compounds was studied individually in non-fasted male Swiss outbred mice weighing 23-33 g. Mice had access to food and water ad libitum throughout the pre- and post-dose sampling period. Compounds were administered orally by gavage (0.1 mL dose volume per mouse) in a suspension of aqueous vehicle (0.5% w/v sodium caboxymethylcellulose, 0.5% v/v benzyl alcohol and 0.4% v/v Tween 80). A single blood sample was collected from each mouse via cardiac puncture at each indicated time point and transferred to heparinised tubes. Blood samples were centrifuged immediately, supernatant plasma was removed and stored at −20° C. until analysis (within 1-2 weeks).

Plasma samples were assayed by LC-MS following protein precipitation with acetonitrile and the concentration of drug in plasma was determined. Pharmacokinetic parameters were calculated on the basis of plasma concentration-time profiles that used the mean plasma concentration at each sample time.

As shown by the graph in FIG. 1A, for a representative compound ((5-Methyl-[1,2,4]triazolo[1,5-a]pyrimidin-7-yl)-(4-trifluoromethyl-phenyl)-amine), administered orally at 20 mg/kg and 50 mg/kg, peak plasma concentrations of 11 and 31 micro molar were obtained respectively. The apparent half-life of trifluorophenyl analog is 108 min at 20 mg/kg and 177 min at 50 mg/kg. Moreover, trifluorophenyl analog is relatively stable with a plasma concentration above 1 µM for 16 hrs following the 50 mg/kg dose. No adverse reactions were observed following oral administration of trifluorophenyl analog at the doses used in this study. Some evidence of nonlinear (dose-dependent) pharmacokinetics is observed for a number of PK parameters. For example, $C_{max}$ increase 3.5 fold for a 2.5-fold increase in (from 7.9±2.5 µM at 20 mg/kg to 27.6±5.0 µM at 50 mg/kg), and the AUC0-last, increased 4.4-fold for a 2.5-fold increase in dose (from 2690 min·µM at 20 mg/kg to 11757 min·µM at 50 mg/kg). Taken together, these results implicate good plasma exposure.

IV. In Vivo Evaluation of Compound Efficacy (A) The standard P. berghei mouse model for infection is utilized to evaluate the efficacy of candidate compounds, according to the invention, against parasites in vivo. See review of Fidock, et al. (2004) Nature Rev. Drug Discovery 3, 509-20. Compounds are dosed either orally or IP, with the exact regimens (e.g. frequency of dosing, drug concentrations at dosing) determined based on the pharmocokinetic profiles of the individual analogs. As shown in FIG. 1B the trifluorophenyl analog suppresses parasite growth when administered to mice orally at 50 mg/kg. Inhibition of parasite growth is determined microscopically by staining a thin smear of blood obtained from the test animal using a Wright-Giemsa stain. Greater suppression of parasite growth is observed if drug is administered twice a day rather than a single dose. These results indicate that the substituted pyrimidyltriazole analogs are potent inhibitors of PfDHODH enzyme and are candidate therapeutics for the treatment of malaria.

(B) In the event that the mouse model does not provide a positive indication for a given candidate compound, a typical course of action is to determine whether P. berghei grown in vitro, in short term culture, is sensitive to the candidate. If sensitivity of P. berghei proves to be the key issue, then a genetically altered P. berghei strain, containing the P. falciparum DHODH enzyme, is generated for the in vivo testing. See Braks, et al. (2006) Nucleic Acids Res. 34, e39, and Janse, et al. (2006) Mol. Biochem. Parasitol. 145, 60-70. Alternatively, the humanized malarial mouse model is used for the testing, in accordance with Morosan, et al. (2006) J. Infect. Dis. 193, 996-1004.

We claim:

1. A compound according to Formula I

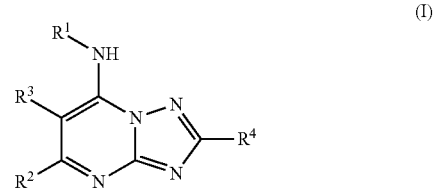

(I)

or a pharmaceutically acceptable salt, stereoisomer, or tautomer thereof, wherein $R^1$ is selected from the group consisting of ($C_6$-$C_{14}$) heterocycloalkyl, ($C_6$-$C_{14}$)aryl, and ($C_6$-$C_{14}$)heteroaryl, wherein when $R^1$ is phenyl, $R^1$ is substituted with one or more substituents selected from the group consisting of ($C_1$-$C_8$)alkyl, ($C_2$-$C_8$)alkenyl, ($C_2$-$C_8$) alkynyl, aryl, heterocycle, ($C_1$-$C_8$)haloalkyl, —Cl, —Br, —I, —CN, —NO$_2$, heteroaryl, and ($C_1$-$C_6$) hydroxyalkyl;

$R^2$ are independently selected from the group consisting of halogen, ($C_1$-$C_8$)alkyl, ($C_2$-$C_8$)alkenyl, ($C_2$-$C_8$) alkynyl, ($C_1$-$C_8$)alkoxy, and ($C_1$-$C_8$)haloalkyl;

$R^3$ are independently selected from the group consisting of hydrogen, halogen, ($C_1$-$C_8$)alkyl, ($C_2$-$C_8$)alkenyl, ($C_2$-$C_8$)alkynyl, ($C_1$-$C_8$)alkoxy, and ($C_1$-$C_8$)haloalkyl;

$R^4$ is selected from the group consisting of halogen, ($C_1$-$C_8$)alkyl, ($C_2$-$C_8$)alkenyl, ($C_2$-$C_8$)alkynyl, ($C_1$-$C_8$)alkoxy, and ($C_1$-$C_8$)haloalkyl;

wherein any heterocycloalkyl, aryl or heteroaryl is optionally substituted with one or more members selected from the group consisting of halogen, —CN, —NO$_2$, hydroxyl, ($C_1$-$C_8$)alkyl, ($C_2$-$C_8$)alkenyl, ($C_2$-$C_8$)alkynyl, ($C_1$-$C_4$)alkoxy, ($C_1$-$C_4$)haloalkyl, and ($C_2$-$C_4$)hydroxyalkyl.

2. The compound of claim 1 that is selected from the group consisting of

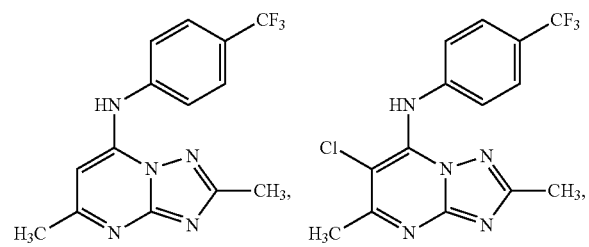

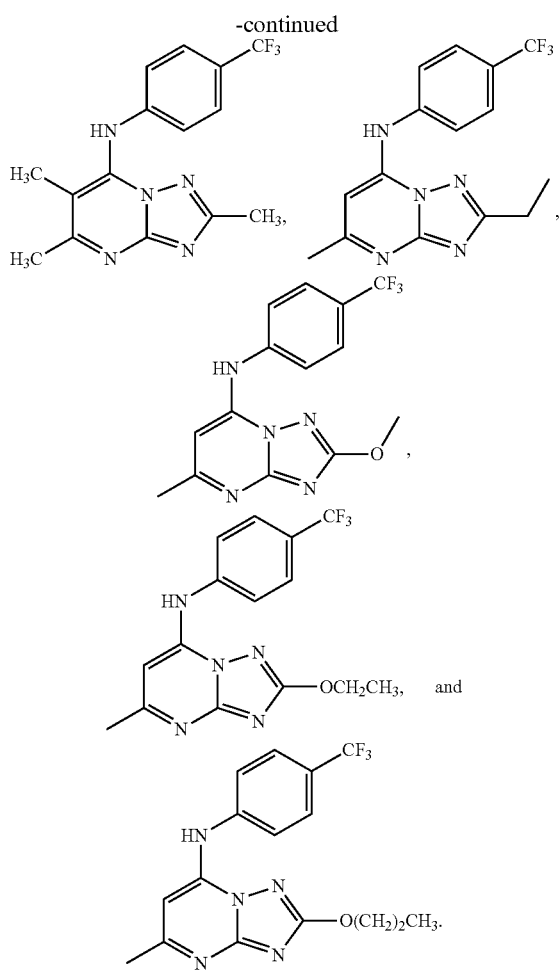

3. A pharmaceutical composition comprising
 (a) a compound of claim 1 or a pharmaceutically acceptable salt, stereoisomer or tautomer thereof; and
 (b) a pharmaceutically acceptable carrier.

4. A method of inhibiting dihydroororate dehydrogenase in a parasite, comprising contacting said parasite with a compound of claim 1.

5. The method of claim 4, wherein the parasite is *Plasmodium falciparum*.

6. A compound of claim 1, selected from the group consisting of:

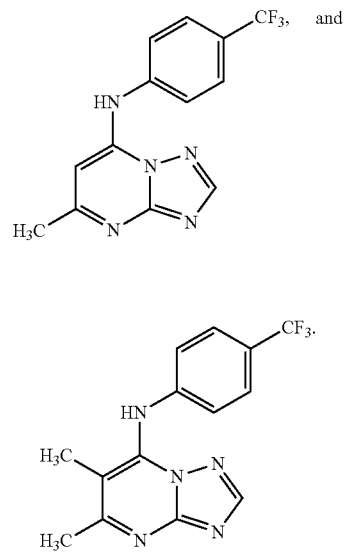

7. The compound of claim 1, wherein the pharmaceutically acceptable salts are selected from alkali metal salts, alkali earth salts, ammonium salts, water-soluble salts or water-insoluble salts.

* * * * *

UNITED STATES PATENT AND TRADEMARK OFFICE
CERTIFICATE OF CORRECTION

PATENT NO. : 9,216,983 B2
APPLICATION NO. : 12/339905
DATED : December 22, 2015
INVENTOR(S) : Margaret Phillips et al.

Page 1 of 2

It is certified that error appears in the above-identified patent and that said Letters Patent is hereby corrected as shown below:

Specification

Column 3,
Line 55, "phenyl, $R^8$" should read --phenyl, $R^{18}$--.

Column 10,
Line 36, "formula -$(CH_2)_n$-X-$(CH_2)_t$-," should read --formula -$(CH_2)_s$-X-$(CH_2)_t$-,--.

Column 18,
Lines 19-22, "2,5-Dimethyl-[1,2,4]triazolo[1,5-o]pyrimidin-7-yl)-naphthalen-2-yl-amine,
2,5-Dimethyl-[1,2,4]triazolo[1,5-x]pyrimidin-7-yl)-anthracen-2-yl-amine"
should read
--2,5-Dimethyl-[1,2,4]triazolo[1,5-α]pyrimidin-7-yl)-naphthalen-2-yl-amine,
2,5-Dimethyl-[1,2,4]triazolo[1,5-α]pyrimidin-7-yl)-anthracen-2-yl-amine--.

Column 23,

Lines 54-59, " 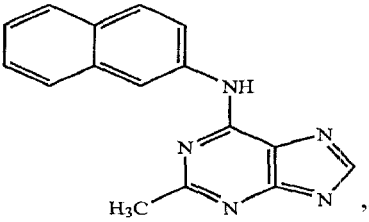 " should read -- 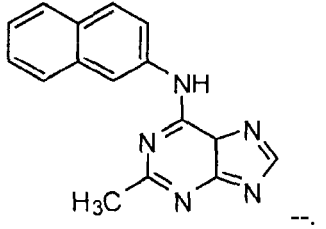 --.

Signed and Sealed this
Fifth Day of July, 2016

Michelle K. Lee
*Director of the United States Patent and Trademark Office*

CERTIFICATE OF CORRECTION (continued)
U.S. Pat. No. 9,216,983 B2

Specification

Column 55,

Lines 15-20, " 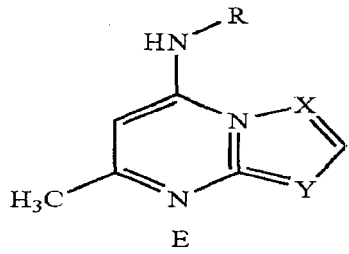 " should read -- 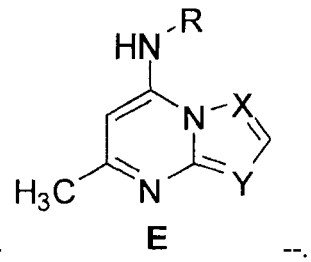 --.

Column 55,
Line 39, "(M + H)" should read --(M + $H^+$)--.

Column 60,
Line 63, "0.315" should read --0.3615--.